US008450094B1

(12) United States Patent
Narendranath et al.

(10) Patent No.: US 8,450,094 B1
(45) Date of Patent: May 28, 2013

(54) SYSTEM FOR MANAGEMENT OF YEAST TO FACILITATE THE PRODUCTION OF ETHANOL

(75) Inventors: Neelakantam V. Narendranath, Sioux Falls, SD (US); David Charles Carlson, Yankton, SD (US)

(73) Assignee: Poet Research, Inc., Sioux Falls, SD (US)

( * ) Notice: Subject to any disclaimer, the term of this patent is extended or adjusted under 35 U.S.C. 154(b) by 358 days.

(21) Appl. No.: 12/717,002

(22) Filed: Mar. 3, 2010

Related U.S. Application Data

(60) Provisional application No. 61/157,151, filed on Mar. 3, 2009.

(51) Int. Cl.
*C12P 7/10* (2006.01)
*C12P 7/08* (2006.01)
*C12P 7/06* (2006.01)
*C12P 7/00* (2006.01)

(52) U.S. Cl.
USPC .......................................... 435/161; 435/132

(58) Field of Classification Search
None
See application file for complete search history.

(56) References Cited

U.S. PATENT DOCUMENTS

| | | |
|---|---|---|
| 2,440,925 A | 5/1948 | Boeckeler |
| 3,940,492 A | 2/1976 | Ehnstrom |
| 4,009,074 A | 2/1977 | Walon |
| 4,092,434 A | 5/1978 | Yoshizumi et al. |
| 4,243,750 A | 1/1981 | Muller et al. |
| 4,279,747 A | 7/1981 | Chen |
| 4,287,303 A | 9/1981 | Dahlberg et al. |
| 4,309,254 A | 1/1982 | Dahlstrom et al. |
| 4,316,956 A | 2/1982 | Lutzen |
| 4,358,536 A | 11/1982 | Thorsson et al. |
| 4,361,651 A | 11/1982 | Keim |
| 4,376,163 A | 3/1983 | Ehnstrom |
| 4,460,687 A | 7/1984 | Ehnstrom |
| 4,474,883 A | 10/1984 | Yamamoto et al. |
| 4,490,469 A | 12/1984 | Kirby et al. |
| 4,514,496 A | 4/1985 | Yoshizumi et al. |
| 4,522,920 A | 6/1985 | Thorsson et al. |
| 4,540,663 A | 9/1985 | Witt |
| 4,591,560 A | 5/1986 | Kainuma et al. |
| 4,618,579 A | 10/1986 | Dwiggins et al. |
| 4,716,218 A | 12/1987 | Chen et al. |
| 4,727,026 A | 2/1988 | Sawada et al. |
| 4,760,025 A | 7/1988 | Estell et al. |
| 4,863,864 A | 9/1989 | Ashikari et al. |
| 4,876,196 A | 10/1989 | Salzbrunn et al. |
| 4,933,279 A | 6/1990 | Carroll et al. |
| 5,061,497 A | 10/1991 | Thacker et al. |
| 5,084,385 A | 1/1992 | Ashikari et al. |
| 5,087,417 A | 2/1992 | Dumbroff et al. |
| 5,177,008 A | 1/1993 | Kampen |
| 5,177,009 A | 1/1993 | Kampen |
| 5,180,669 A | 1/1993 | Antrim |
| 5,231,017 A | 7/1993 | Lantero et al. |
| 5,250,182 A | 10/1993 | Bento et al. |
| 5,260,089 A | 11/1993 | Thornberg |
| RE34,606 E | 5/1994 | Estell et al. |
| 5,322,778 A | 6/1994 | Antrim et al. |
| 5,364,770 A | 11/1994 | Berka et al. |
| 5,545,543 A | 8/1996 | Zinnamosca et al. |
| 5,559,031 A | 9/1996 | Zinnamosca et al. |
| 5,652,127 A | 7/1997 | Mitchinson et al. |
| 5,688,674 A | 11/1997 | Choi et al. |
| 5,721,127 A | 2/1998 | Deweer et al. |
| 5,721,128 A | 2/1998 | Deweer et al. |
| 5,736,375 A | 4/1998 | Deweer et al. |
| 5,736,499 A | 4/1998 | Mitchinson et al. |
| 5,756,714 A | 5/1998 | Antrim et al. |
| 5,817,498 A | 10/1998 | Deweer et al. |
| 5,824,532 A | 10/1998 | Barnett et al. |
| 5,849,549 A | 12/1998 | Barnett et al. |
| 5,958,739 A | 9/1999 | Mitchinson et al. |
| 5,981,237 A | 11/1999 | Meagher et al. |
| 6,074,854 A | 6/2000 | Deweer et al. |
| 6,136,576 A | 10/2000 | Diaz-Torres et al. |
| 6,171,817 B1 | 1/2001 | Berka et al. |
| 6,228,177 B1 | 5/2001 | Torget |
| 6,313,328 B1 | 11/2001 | Ulrich et al. |
| 6,423,145 B1 | 7/2002 | Nguyen et al. |

(Continued)

FOREIGN PATENT DOCUMENTS

| | | |
|---|---|---|
| CA | 1143677 | 3/1983 |
| DE | 267508 | 5/1989 |

(Continued)

OTHER PUBLICATIONS

Jeffries et al, Biotechnol. & Bioengin. 31: 502 (1988).*
U.S. Appl. No. 12/716,989, filed Mar. 3, 2010, Kwiatkowski et al.
U.S. Appl. No. 12/717,002, filed Mar. 3, 2010, Narendranath et al.
Abouzied et al., "Direct fermentation of potato starch to ethanol by cocultures of *Aspergillus niger* and *Saccharomyces cerevisiae*", Appl Environ Microbiol, 1986, 52(5):1055-9.
Aden et al., "Lignocellulolsic biomass to ethanol process design and economics utilizing co-current dilute acid prehydrolysis and enzymatic hydrolysis for corn stover", NREL, NREL-TP-510-32438, 2002, pp. 1-88 and Appendices A-G.
Aldrich, "New enzymes lower ethanol production fuel costs", BridgeNews, Kansas City, 2004.

(Continued)

*Primary Examiner* — James Martinell
(74) *Attorney, Agent, or Firm* — Foley & Lardner LLP

(57) ABSTRACT

A system and method for managing an ethanologen for use in biorefinery is disclosed. The method for propagating ethanologen for use in the production of a fermentation product from biomass omprises the steps of providing a medium for propagation of ethanologen and supplying a first cell mass of ethanologen to the medium. A first cell mass of ethanologen is propagated into a larger second cell mass of ethanologen. The system for propagating ethanologen for use in the production of a fermentation product from biomass comprises a first stage comprising a first vessel configured to maintain a medium comprising ethanologen and a second stage comprising a second vessel configured to maintain a medium supplied from the first stage.

53 Claims, 20 Drawing Sheets

U.S. PATENT DOCUMENTS

| | | | |
|---|---|---|---|
| 6,451,063 | B1 | 9/2002 | Clarkson et al. |
| 6,509,180 | B1 | 1/2003 | Verser et al. |
| 6,538,182 | B1 | 3/2003 | Thompson et al. |
| 6,616,948 | B2 | 9/2003 | Gustavsson et al. |
| 6,664,095 | B1 | 12/2003 | Suryanarayan et al. |
| 6,709,527 | B1 | 3/2004 | Fechter et al. |
| 6,774,284 | B1 | 8/2004 | Thompson et al. |
| 6,803,218 | B1 | 10/2004 | Seyfried et al. |
| 6,849,439 | B2 | 2/2005 | Henson et al. |
| 6,849,782 | B2 | 2/2005 | Thompson et al. |
| 6,855,529 | B2 | 2/2005 | Thompson et al. |
| 6,867,237 | B1 | 3/2005 | Taylor et al. |
| 6,878,860 | B1 | 4/2005 | Thompson et al. |
| 7,344,876 | B2 * | 3/2008 | Levine ........................ 435/255.1 |
| 7,579,177 | B2 | 8/2009 | Olsen et al. |
| 7,622,284 | B2 | 11/2009 | Op Den Camp et al. |
| 2003/0134395 | A1 | 7/2003 | Shetty et al. |
| 2003/0134396 | A1 | 7/2003 | Shetty et al. |
| 2003/0180900 | A1 | 9/2003 | Lanteo |
| 2003/0203454 | A1 | 10/2003 | Chotani et al. |
| 2004/0023349 | A1 | 2/2004 | Bisgaard-Frantzen et al. |
| 2004/0043117 | A1 | 3/2004 | Cope et al. |
| 2004/0063184 | A1 | 4/2004 | Grichko |
| 2004/0080923 | A1 | 4/2004 | Janisch |
| 2004/0091983 | A1 | 5/2004 | Veit et al. |
| 2004/0115779 | A1 | 6/2004 | Olsen et al. |
| 2004/0157301 | A1 | 8/2004 | Chotani et al. |
| 2004/0192896 | A1 | 9/2004 | Finch |
| 2004/0197409 | A1 | 10/2004 | Iyer et al. |
| 2004/0219649 | A1 | 11/2004 | Olsen et al. |
| 2004/0234649 | A1 | 11/2004 | Lewis et al. |
| 2005/0026261 | A1 | 2/2005 | Otto et al. |
| 2005/0042737 | A1 | 2/2005 | Vikso-Nielsen et al. |
| 2005/0100996 | A1 | 5/2005 | Lantero, Jr. et al. |
| 2005/0136525 | A1 | 6/2005 | Baldwin et al. |
| 2005/0208623 | A1 | 9/2005 | Baldwin et al. |
| 2005/0233030 | A1 | 10/2005 | Lewis et al. |
| 2005/0239181 | A1 | 10/2005 | Lewis et al. |
| 2006/0051847 | A1 * | 3/2006 | Gunnarsson et al. .......... 435/134 |
| 2006/0246563 | A1 * | 11/2006 | Eroma et al. .................. 435/158 |
| 2007/0178567 | A1 | 8/2007 | Lewis |
| 2007/0196907 | A1 | 8/2007 | Lewis |
| 2007/0202214 | A1 | 8/2007 | Lewis et al. |
| 2008/0032373 | A1 | 2/2008 | Bhargava et al. |
| 2009/0053793 | A1 | 2/2009 | Lefebvre et al. |
| 2010/0041116 | A1 | 2/2010 | Lewis et al. |
| 2010/0151549 | A1 | 6/2010 | Bhargava et al. |
| 2010/0196980 | A1 | 8/2010 | Smith et al. |
| 2010/0227369 | A1 | 9/2010 | Narendranath et al. |
| 2010/0233771 | A1 | 9/2010 | McDonald et al. |
| 2011/0070618 | A1 | 3/2011 | Lewis |
| 2011/0097446 | A1 | 4/2011 | Lewis |
| 2011/0111085 | A1 | 5/2011 | Lewis et al. |
| 2011/0250312 | A1 | 10/2011 | Lewis |

FOREIGN PATENT DOCUMENTS

| | | |
|---|---|---|
| EP | 0138428 | 4/1985 |
| EP | 0 140 410 | 5/1985 |
| EP | 0 171 218 | 2/1986 |
| GB | 2089836 | 12/1981 |
| JP | 58-005145 | 1/1983 |
| JP | 59-179093 | 10/1984 |
| WO | WO 91/03543 | 3/1991 |
| WO | WO 92/20777 | 11/1992 |
| WO | WO 95/13362 | 5/1995 |
| WO | WO 97/27047 | 7/1997 |
| WO | WO 02/38787 | 5/2002 |
| WO | WO 02/074895 | 9/2002 |
| WO | WO 03/018766 | 3/2003 |
| WO | WO 03/062430 | 7/2003 |
| WO | WO 03/066816 | 8/2003 |
| WO | WO 03/066826 | 8/2003 |
| WO | WO 03/068976 | 8/2003 |
| WO | WO 2004/080923 | 9/2004 |
| WO | WO 2004/081193 | 9/2004 |
| WO | WO 2004/106533 | 12/2004 |
| WO | WO 2005/052148 | 6/2005 |
| WO | WO 2005/082155 | 9/2005 |

OTHER PUBLICATIONS

Allison et al., "Transformation of the thermophilic fungus humicola grisea var. thermoidea and overproduction of humicola glucoamylase", Curr Genet, 1992, 21:225-229.

Argus Leader.Com., Web Page—Business—Broin Goes to Court, Printed Jun. 27, 2006, pp. 1-3.

Ashikari et al., "rhizopus raw-starch-degrading glucoamylase: its cloning and expression in yeast", Agric. Bio. Chem., 1986, 50(4):957-964.

Author Unknown "Ready for Research", BioFuels Journal, pp. 20-23 (4Q04).

Author Unknown, "Alcohol and Alcohol Derivative", Chematur Engineering AB, (Internet Mar. 2003).

Author Unknown, "Chapter 1. Review of the literature—coproducts and near coproducts of fuel ethanol fermentation from grain", Agriculture and Agri-Food Canada Research Branch (Internet Mar. 2003).

Author Unknown, "Determination of acid α-Amylase activity, FIA", SOP No. EB-SM-0259.02/01 pp. 1-14 (Internet Mar. 2003).

Author Unknown, "Determination of amyloglucosidase activity using the auto analyzer", Novozymes Analytical Method EB-SM-0131.02/01 (Internet Mar. 2003).

Author Unknown, "Enzymatic modification of starch granules: peeling off versus porosity", TNO Nutrition and Food Research, Dec. 28, 2000, pp. 1-2.

Author Unknown, "Grain processing enzymes for sweetener production", Genencor International. Apr. 2004, pp. 1-3.

Author Unknown, "Novelose® resistant starch—the starch that thinks it's a fiber", National Starch and Chemical Compnay, 2003.

Author Unknown, "Nutrient composition of DDGS (100% dry matter basis) from various references—Table 1", Distillers Grains Quarterly, First Quarter 2006, pp. 27-28.

Author Unknown, "SIU Edwardsville National corn to ethanol research pilot plant process description", Project No. 24307-78188, Washington group, Nov. 12, 2001.

Author Unknown, "Spirizyme Plus for ethanol production", Novozymes Application Sheet Ethanol/2002-03379-03.pdf (Internet Mar. 2003).

Author Unknown, "Very high gravity technology", Ethanol Producer Magazine, Jan. 2006.

Bardini et al., "Continuous clarification of grape must by flotation," Vini d'italia, 1992, 34(1):31-38, Abstract.

Belya et al., "Composition of corn and distillers dried grains with solubles from dry grind ethanol processing", Bioresource Technology, 2004, 94:293-298.

Berven, "The Making of Broin Project ", Ethanol Producer Magazine, Feb. 2005, pp. 66-71.

Biotimes: The enzyme e-zine, "Fuel Ethanol Products" (Jan. 2003).

Biswas et al., "Analysis of Headspace Compounds of Distillers Grains using SPME in Conjunction with GC/MS and TGA", Journal of Cereal Science, 2001, 33:223-229.

Boel et al., "Glucoamylases G1 and G2 from *Aspergillus niger* are synthesized from two different but closely related mRNAs", The EMBO Journal, 1984, 3(5):1097-1102.

Bothast, "Ethanol research facility one of a kind," Industrial Oil Products Article, 2004, 15(8):518-519.

Brown et al., "The effect of temperature on the ehtanol tolerance of the yeast, *Saccharomyces uvarum*", Biotechnology Letters, 1982, 4(4):269-274.

Bryan, "Changing the Game", Ethanol Producer Magazine, Aug. 2005, pp. 58-63.

Carlson, M., "Distillers By-Products for Swine Diets", Missouri Value Added Development Center, Internet Mar. 2003.

Casey et al., "Reevaluation of Alcohol Synthesis and Tolerance on Brewer's Yeast", American Society of Brewing Chemists, Inc., 1985, 43(2):75-83.

Chen et al., "Comparison of four different chemical pretreatments of corn stover for enhancing enzymatic digestibility." Biomass and Bioenergy, 2009, 33:1381-1385.

Chen et al., "Effect of replacing helical glycine residues with alanines on reversible and irreversible stability and production of *Aspergillus awamori* glucoamylase", Protein Engineering, 1996, 9(6):499-505.

Chi et al., "High-concentration alcoholic production from hydrolysate of raw ground corn by a tetraploid yeast strain", Biotechnolgy Letters, 1993, 15(8):877-882.

Civil Docket for Case No. 4:04-cv-04202-LLP printed Jun. 23, 2006.

PCT/US04/07377 International Search Report dated Jun. 1, 2005.

PCT/US2005/008155 International Search Report Dated Nov. 30, 2005 and Written Opinion.

Daugulis et al., "The Economics of Ethanol Production by Extractive Fermentation", The Canadian Journal of Chemical Engineering, 1991, 69:488-497.

De Mancilha et al., "Evaluation of Ion Exchange Resins for Removal of Inhibitory Compounds from Corn Stover Hydrolyzate for Xylitol Fermentation", Biotechnology Progress, 2003, vol. 19, pp. 1837-1841.

Dettori-Campus et al., "Hydrolysis of Starch Granules by the Amyase from *Bacillus stearothermophilus* NCA 26", Process Biochemistry, 1992, 27:17-21.

District Court Civil Docket No. 1: Complaint, filed by Broin and Associates, Inc., Entered: Dec. 15, 2004.

District Court Civil Docket No. 102: Genencor's Notice to Take Deposition of Novozymes North America, Inc., Entered May 2, 2005.

District Court Civil Docket No. 112: Transcript of Proceedings held on Mar. 4, 2005 regarding Docket No. 69, motion Hearing, Entered: May 13, 2005.

District Court Civil Docket No. 132: Memorandum Opinion and Order regarding Docket No. 54, denying in part Motion to Dismiss as to Counts III, IV, V, and VIII and granting without prejudice to Plaintiff's right to amend as to Counts VI and VII, denying Docket No. 54, Motion for a more Definite Statement Signed by Judge Lawrence L. Piersol on Jul. 26, 2005, Entered: Jul. 26, 2005.

District Court Civil Docket No. 138: Genencor International, Inc.'s Answer to Amended Complaint and Counterclaim against Broin and Associates, Inc., by Genencor International, inc. Entered: Aug. 29, 2005.

District Court Civil Docket No. 148: Reply to Docket No. 138, Answer to Amended Complaint and Counterclaim against filed by Broin and Associates, Inc., Broin and Associates, Inc. Entered: Sep. 20, 2005.

District Court Civil Docket No. 15-1: First Amended Complaint, filed by Broin and Associates, Inc. (Attachments: #1 Exhibit A—Press Release #2 Exhibit B—Magazine Article), Entered Jan. 25, 2005.

District Court Civil Docket No. 15-2: Press Release dated Nov. 4, 2004, Broin Companies Announces Ethanol Technology Revolution.

District Court Civil Docket No. 153: Memorandum in Support regarding Docket No. 152, Motion to dismiss First Amended Complaint Based on Intentional Violations of Protective Order filed by Genencor International, Inc. (Sanford, Steven) (Entered: Sep. 30, 2005).

District Court Civil Docket No. 16: First Motion to Expedite Discovery and Supporting Brief by Broin and Associates, Inc., Entered: Jan. 25, 2005.

District Court Civil Docket No. 17-1: Declaration of Jeffrey C. Brown regarding (16) First Motion to Expedite Discovery and Supporting Brief, Entered: Jan. 25, 2005.

District Court Civil Docket No. 17-6: Exhibit E of Docket No. 17, Plaintiff's First Set of Interrogatories to Defendant, Entered: Jan. 25, 2005.

District Court Civil Docket No. 50-1: Affidavit of Steven W. Sanford in Support of Defendant Genencor's Opposition to Motion for Summary Judgment, Entered Feb. 14, 2005.

District Court Civil Docket No. 50-6: Exhibit D of Docket No. 50, Jan. 10, 2005 letter from Mark Skoog to Ben Brown, Entered: Feb. 14, 2005.

District Court Civil Docket No. 52: Memorandum in Opposition regarding Docket No. 16, First Motion to Expedite Discovery and Supporting Brief, filed by Genencor International, Inc., Entered: Feb. 14, 2005.

District Court Civil Docket No. 53: Motion for Discovery, Requiring Plaintiff to Specify Trade Secrets Prior to Commencement of Discovery and Supporting Brief, b y Genencor International, Inc. Entered: Feb. 14, 2005.

District Court Civil Docket No. 54: Motion to Dismiss Pursuant to FRCP 12(b)(6); Motion for a More Definite Statement Pursuant to FRCP 12(e) and Supporting Brief, by Genencor International, Inc., Entered: Feb. 14, 2005.

District Court Civil Docket No. 61: Response to Motion regarding Docket No. 53, Motion for Discovery, Requiring Plaintiff to Specify Trade Secrets Prior to Commencement of Discovery and Supporting Brief, filed by Broin and Associates, Inc., Entered: Feb. 28, 2005.

District Court Civil Docket No. 62: Reply to Motion Response regarding Docket No. 16, First Motion to Expedite Discovery and Supporting Brief, filed by Broin and Associates, Inc., Entered: Mar. 1, 2005.

District Court Civil Docket No. 67: Reply to Motion Response regarding Docket No. 53, Motion for Discovery, Requiring Plaintiff to Specify Trade Secrets Prior to Commencement of Discovery and Supporting Brief, filed by Genencor International, Inc. Entered: Mar. 2, 2005.

District Court Civil Docket No. 68: Form 35 Report of parties Planning Meeting and Scheduling Information, Entered: Mar. 3, 2005.

District Court Civil Docket No. 77: Memorandum in Opposition regarding Docket No. 54, Motion to Dismiss Pursuant to FRCP 12(b)(6); Motion for a More Definite Statement Pursuant to FRCP 12(e) and Supporting Brief, filed by Broin and Associates, inc. Entered: Mar. 9, 2005.

District Court Civil Docket No. 85: Reply to Motion Response regarding Docket No. 54, Motion to Dismiss Pursuant to FRCP 12(b0(6); Motion for a More Definite Statement Pursuant to FRCP 12(e) and Supporting Brief, filed by Genencor International, Inc., Entered: Mar. 23, 2005.

District Court Civil Docket No. 90: Response to Docket No. 87 Brief, Regarding Genencor's Objections to Broin's Identification of Trade Secrets, filed by Broin and Associates, inc., Entered: Apr. 11, 2005.

District Court Civil Docket No. 95: Form 35 Report of Parties Planning Meeting and Scheduling information, Entered: Apr. 18, 2005.

Dong et al., "The Neutral Detergent Fiber, Acid Detergent Fiber, Crude Fiber, and Lignin Contents of Distillers' Dried Grains with Solubles", Journal of Food Science, 1987, 52(2):403-405.

Donohoe et al., "Detecting cellulase penetration into corn stover cell walls by immuno-electron microscopy", Biotechnology and Bioengineering, 2009, 103(3):480-489.

Dunn-Coleman et al., "Production of granular starch hydrolyzing enzymes for low energy grain ethanol production", 27th Symposium on Biotechnology for Fuels and Chemicals, Genencor International Presentation, (May 2005).

Elander et al., "Summary of findings from the Biomass Refining Consortium for Applied Fundamentals and Innovation (CAFI): corn stover pretreatment", Cellulose, 2009, 16:649-659.

International Search Report in PCT/US2006/017041 mailed Sep. 15, 2006.

Extended European Search Report dated Oct. 29, 2012 in related European Application Serial #12184429.4.

Form PCT/ISA/220, International Search Report and Written Opinion of International Patent Application PCT/US2005/008156, dated Mar. 7, 2006.

Fox, Fermentation and Biochemical Engineering Handbook Principles, Process Design, and Equipment, Second Edition, Vogel et al (eds.). Noyes Publications, Westwood, New Jersey, 1997, pp. 734-758.

Fujio et al., "Alcohol Fermentation of Raw Cassava Starch by Rhizopus koji without cooking", Biotechonolgy and Bioengineering, 1984, 26:315-319.

Fujio et al., "Ethanol Fermentation of Raw Cassava Starch with Rhizopus koji in a Gas Circulation Type Fermentor", Biotechnology and Bioengineering, 1985, 27:1270-1273.

GCOR Lantero patent application search USPTO site. May 17, 2005.

Genencor Inventor Search, Oct. 3, 2005.

Gulati et al., "Assessment of Ethanol Production Options for Corn Products", Bioresource Technology, 1996, vol. 58, pp. 253-264.

Hamdy et al., "Effects of virginiamycin on fermentation rate by yeast", Biomass and Bioenergy, 1996, 11(1):1-9.

Hamelinck et al., "Ethanol from lignocellulosic biomass: techno-economic performance in short-, middle- and long term", Biomass and Bioenergy, 2005, 28:384-410.

Han et al., "Saccharification and Ethanol Fermentation from Uncooked Starch Using *Aspergillus niger* Koji", Korean J. Food Sci. Technol., 1985, 17(4):258-264.

Han et al., "Amylolysis of Raw Corn by *Aspergillus niger* for Simultaneous Ethanol Fermentation", Biotechnology and Bioengineering, 1987, 30:225-232.

Hayashida et al., "High Concentration-Ethanol Fermantation of Raw Ground Corn", Agric. Biol. Chem., 1982, 46(7):1947-1950.

Hayashida et al., "Molecular cloning of Glucoamylase 1 Gene of *Aspergillus awamori* var. kawachi for Localization of the Raw-starch-affinity Site", Agric. Biol. Chem., 1989, 53(4):923-929.

Hayashida et al., "Raw Starch-digestive Glucoamulase Productivity of Protease-less Mutant from Asoergukkys awaniru var. kawachi", Agric. Biol. Chem., 1981, 45(12):2675-2681.

Honeyman et al., "Evaluation of a Distillers Dried Grain Derivative Feedstuff on Performance of Nursery Pigs", Iowa State University, Nutrition (Internet Mar. 2003).

Islam et al., "Stability of virginiamycin and penicillin during alcohol fermentation", Biomass and Bioenergy, 1999, 17: 369-376.

Iwata et al. "Purification and Characterization of Rice α-glucosidase, a key enzyme for Alcohol Fermentation of Rice Polish", Journal of Bioscience and Bioengineering, 2003, 95(1):106-108.

Jacques et al., The Alcohol Textbook, 3rd Edition, a reference for the beverage, fuel and industrial alcohol industries, Nottingham University Press 1999, Alltech Inc. 1999 (386 pages).

Jacques et al., The Alcohol Textbook, 4th Edition, a reference for the beverage, fuel and industrial alcohol industries, Nottingham University Press 2003 Alltech Inc. 2003 (446 pages).

Jensen et al., "Purification of extracellular amylolytic enzymes from the thermophilic fungus Thermomyces lanuginosus", Can. J. Microbiol., 1988, 34:218-223.

Jones, "review: Biological principles for the effects of ethanol", Enzyme Microb. Technol., 1989, 11:130-153.

Joutsjoki et al., "A Novel Glucoamylase Preparation for Grain Mash Saccharification", Biotechnology Letters, 1993, 15(3):227-282.

Kang et al., "Effect of Initiation Factor eIF-5A Depletion on Protein Synthesis and Proliferation of *Saccharomyces cerevisiae*", J. Biol. Chem., 1994, 269(6):3934-3940.

Knott et al., "Effects of the Nutrient Variability of Distiller's Solubles and Grains within Ethanol Plants and the Amount of Distiller's Solubles Blended with Distiller's Grains on Fat, Protein and Phosphorus Content of DDGS", 2004.

Knott et al., "Variation in Particle Size and Bulk Density of Distiller's Dried Grains with Solubles (DDGS) Produced by "New Generation" Ethanol Plants in Minnesota and South Dakota", 2004.

Kuyper et al., "Evolutionary engineering of mixed-sugar utilization by a xylose-fermenting *Saccharomyces cerevisiae* strain", FEMS Yeast Research, 2005, 5:925-934.

Lang et al., "Recycle Bioreactor for Bioethanol Production from Wheat Starch II. Fermentation and Economics", Energy Sources, 2001, 23:427-436.

Lutzen, "Enzyme Technology in the Production of Ethanol—Recent Process Development", Advances in Biotechnology, vol. II: Fuels, Chemicals, Foods and Waste Treatment, 1981 Pergamon Pres Canada Ltd., pp. 161-167.

Ma et al., "Alcohol production from starch by mixed cultures of *Aspergillus awamori* and immobilized *Saccharomyces cerevisiae* a different agitation speeds", J. Basic Microbio, 2002, 42(3):162-71, Abstract.

Makarov et al., "Quality improvement of table wines following continuous clarification treatments," Kharachova Promislovist, 1976, Abstract only.

Matsumoto et al., "Industrialization of a Noncooking System for Alcoholic Fermantation from Grains", Agric. Biol. Chem., 1982, 46(6):1549-1558.

Matsuoka et al., "Alcoholic Fermentation of Sweet Potato without Cooking", J. Ferment. Technol., 1982, 60(6):599-602.

McAloon et al., "Determining the Cost of Producing Ethanol from Corn Starch and Lignocellulosic Feedstocks", Technical Report NRELTP-580-28893, 2000, www.doe.gov/bridge.

McLean et al., "Fluorometric Method for Measuring Yeast Metabolic Activity", Technical Report, 2002, 3:5-25.

McLean et al., "A Novel Method for Quantitation of Active Yeast Cells", Technical Report, 2001, 2:1-5.

Mikuni et al., "Alcohol Fermentation of Corn Starch Digested by Chalara paradoxa Amylase without Cooking", Biotechnology and Bioengineering, 1987, 29:729-732.

Minnesota Pollution Control Agency, Ethanol Production in Minnesota. Air Quality/ General #1.20/ Oct. 2002, pp. 1-4.

Morris et al., "AFM Images of Complexes between Amylose and *Aspergillus niger* Glucoamylase Mutants, Native and Mutant Starch Binding Domains: A Model for the Action of glucoamylase", Starch/Starke, 2005, 57:1-7.

Naidu et al., "Effects of Particle Size Reduction on Saccharification in Dry Grind Corn Processing", Department of Agriculture of Biological Engineering, University of Illinois at Urbana Champaign, Poster Presentation 2002 or later.

Narendranath et al., "Acetic Acid Lactic Acid Inhibition of Growth of *Saccharomyces cerevisiac* b Different Mechanisms", American Society of Brewing Chemists, Inc., 2001, 59(4):187-194.

Narendranath et al., "Effect of yeast inoculation rate on the metabolism of contaminating lactobailli during fermentation of corn mash", J. Ind. Microbiol. Biotechnol., 2004, 31:581-584.

Narendranath et al., "Effects of acetic acid and lactic acid on the growth of *Saccharomyces cerevisiae* in minimal medium", Journal of Industrial Microbiology & Biotechnology, 2001, 26:171-177.

Narendranath et al., "Effects of Lactobacilli on Yeast-Catalyzed Ethanol Fermentations", Applied and Environmental Microbiology, 1997, 60(11):4158-4163.

Narendranath et al., "Relationship between pH and Medium Dissolved Solids in Terms of Growth and Metabolism of *Lactobacilli* and *Saccharomyces cerevisiae* during Ethanol Production", Applied and Environmental Microbiology, 2005, 71(5):2239-2243.

Narendranath et al., "Urea Hydrogen Peroxide Reduces the Number of *Laactobacilli*, Nourishes Yeast, and Leaves No Residues in the Ethanol Fermentation", Applied and Environmental Microbiology, 2000, 66(10):4187-4192.

Narita et al., "Efficient Production of L-(+)-Lactic Acid from Raw Starch by *Streptococcus bovis* 148", Journal of Bioscience and Bioengineering, 2004, 97(6):423-425.

Nigam et al., "Enzyme and microbial systems involved in starch processing", Enzyme and Microbial Technology, 1995, vol. 17, pp. 770-778.

Nilvebrandt et al., "Detoxification of Lignocellulose Hydrolysates with Ion-Exchange Resins", Applied Biochemistry and Biotechnology, vols. 91-93, 2001, pp. 35-49.

Patent Title Word Search, Sep. 28, 2005.

PCT Patent Title Word Search, Genencor Assignee, Oct. 4, 2005.

Porter et al., "Variability in Soy Flour Composition", JAOCS, 2003, 80(6):557-562.

Pourbafrani et al., "Production of biofuels, limonene and pectin from citrus wastes", Bioresource Technology, 2010, 101:4246-4250.

Rosentrater, "Understanding Distillers Grain Storage, Handling and Flowability Challenges", Distillers Grain Quarterly, First Quarter 2006, pp. 18-21.

Saha et al., "Raw Starch Absorption, Elution and Digestion Behavior of Glucoamylase of Rhizopus niveus", J. Ferment. Technol., 1983, 61(1):67-72.

Schnier et al., "Translation Initiation Factor 5A and its Hypusine Modification are Essential for Cell Viability in the yeast *Saccharomyces cerevisiae*", Molecular and Cellular Biology, 1991, 11(6):3105-3114.

Shibuya et al., "Molecular Cloning of the Glucoamylase Gene of *Aspergillus shirousami* and its Expression in *Aspergillus oryzae*", Agric. Biol. Chem., 1990, 54(8):1905-1914.

Shleser, "Ethanol Production in Hawaii: Processes, Feedstocks, and Current Economic Feasibility of Fuel Grade Ethanol Produciton in Hawaii", Hawaii State Department of Business, Economic Development & Tourism, Final Report, Jul. 1994.

Shurson, "Overview of Swine Nutrition Research on the Value and Application of Distiller's Dried Grains with Solubles Produced by Minnesota and South Dakota Ethanol Plants", pp. 1-40 (Internet Mar. 2003).

Shurson, "The Value of High-Protein Distillers Coproducts in Swine Feeds", Distillers Grains Quarterly, First Quarter 2006, pp. 22.

Sigmund et al., "The Economics of Fair Play", Scientific American, 2002, pp. 83-87.

Singleton et al., Dictionary of Microbiology and Molecular Biology, 1991. John Wiley and Sons. p. 964, col. I, II. 45-48.

SpringerLink-Article, Web Page—Article—Natural Resources Research—"Ethanol Fuels: Energy Balance, Economics, and Enviornmental Impacts Are Negative", Printed Jul. 5, 2005, pp. 1-2.

Supplementary European Search Report Dated Sep. 21, 2010 in EP application 04719274.5.

Suresh et al., "Production of ethanol by raw starch hydrolysis and fermentation of damaged grains of wheat and sorghum", Bioprocess Engineering, 1999, 21:165-168.

Author Unknown, The fuel of the future, Novozymes (May 2002).

Swanson, Company Spotlight, "Partnering in Progress", Ethanol Producer Magazine, 2004, pp. 62-64, 66-68.

Taherzadeh, et al., Pretreatment of Lignocellulosic Wastes to Improve Ethanol and Biogas Production: A Review, Int. J. Mol. Sci., 9:1621-1651 (2008).

Taylor et al., "Dry-Grind Process for Fuel Ethanol by Continuous Fermentation and Stripping", American Chemical Society and American Institute of Chemical Engineers, accepted for publication Mar. 27, 2000, p. A-G.

Taylor et al., "Some Properties of a Glucoamylase produced by the Thermophilic Fungus Humicola lanuginose", Carbohydrate Research, 1978, 61:301-308.

Thammarutwasik et al., "Alcoholic Fermentation of Sorghum Without Cooking", Biotechnology and Bioengineering, 1986, 28:1122-1125.

Thomas et al., "Fuel Alcohol Production: Effects of Free Amino Nitrogen on Fermentation of Very-High-Gravity Wheat Mashes", Applied and Environmental Microbiology, 1990, 56(7):2046-2050.

Tosi et al., "Purification and characterization of an extracellular glucoamylase from the thermophilic fungus Humicola grisea var. thermoidea", Can J. Microbiol., 1993, 39:846-852.

Tritto, "2 grants, 6 clients boost yields at ethanol center", St. Louis Business Journal, Nov. 26-Dec. 2, 2004.

Ueda et al., "Alchoholic Fermentation of Raw Starch without Cooking by Using Back-koji Amylase", J. Ferment. Technol., 1980, 58(3):237-242.

Ueda et al., "Direct hydrolysis of raw starch", Microbiological Sciences, 1984, 1(1):21-24.

Ueda, "Ethanol Fermentation of Starch Materials without Cooking", J. Jap. Soc. Starch Sci., 1982, 29(2):123-130, (English Abstract).

Van Maris et al., "Alcoholic fermentation of carbon sources in biomass hydrolysates by *Saccharomyces cerevisiae*: current status", Antonie van Leeuwenhoek, 2006, 90:391-418.

Van Uden et al., "Effects of ethanol on yeast performance; targets and underlying mechanisms". European Brewery Convention, Proceedings of the 19$^{th}$ Congress, London 1983, pp. 137-144.

Viitanen et al., "Production of a xylose utilizing *Zymomonas mobilis* strain for ethanol production from high concentrations of mixed sugars", 31st Symposium on Biotechnology for Fuels and Chemicals; San Francisco, CA May 2009, p. 48.

Wang. "Argonne National Laboratory Ethanol Study: Key points." Office of Energy Efficiency and Renewal Energy—U.S. Department of Energy, pp. 1-3, 2005.

Waxy Corn, U.S. Grains Council, pp. 1-8 (Internet Mar. 2003).

Weigel et al., "Feed Co-Products of the Dry Corn Milling Process", Feed Co-Products Handbook, pp. 1-13 (Internet Mar. 2003).

Weiss et al. "Distillers Grains", eXtension, Last Updated May 12, 2009, pp. 1-6, Printed May 8, 2010.

Weller et al., "Fuel Ethanol from Raw Corn by *Aspergilli* Hydrolysis with Concurrent Yeast Fermentation", Biotechnology and Bioengineering Symp., 1983, 13:437-447.

www.nrel.gov/docs/fy02osti/31195.pdf. Biofuels News. vol. 4. No. 3. Fall 2001.

Yue et al., "Functionality of resistant starch in food applications", National Starch & Chemical (reprinted from Dec. 1998 issue of Food Australia) (1999).

Zheng et al., "Enzymatic saccharification of dilute acid pretreated saline crops for fermentable sugar production", Applied Energy, 2009, 86:2459-2465.

Ziffer et al., "Temperature Effects in Ethanol Fermentation High Corn Media", Biotechnology Letters, 1982, 4(12):809-814.

Beesabathuni. "Effect of Corn Flour Particle Size on Ethanol Yield and Soluble Solids in Thin Stillage in a Dry Grind Process." American Society of Agricultural and Biological Engineers, Paper No. 036067, 2003.

\* cited by examiner

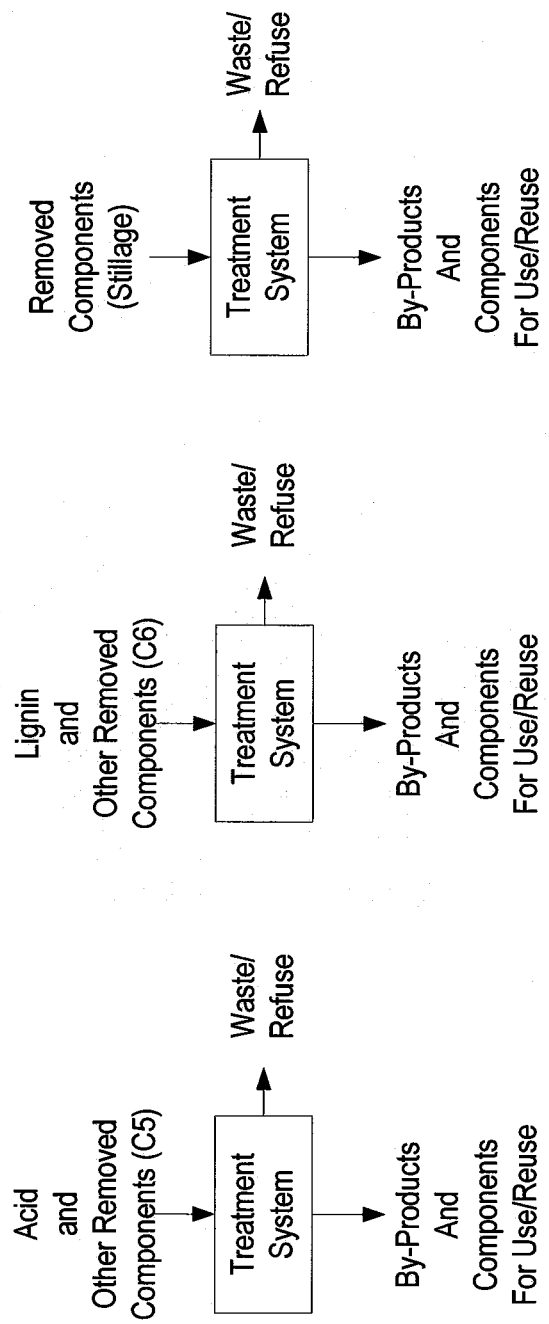

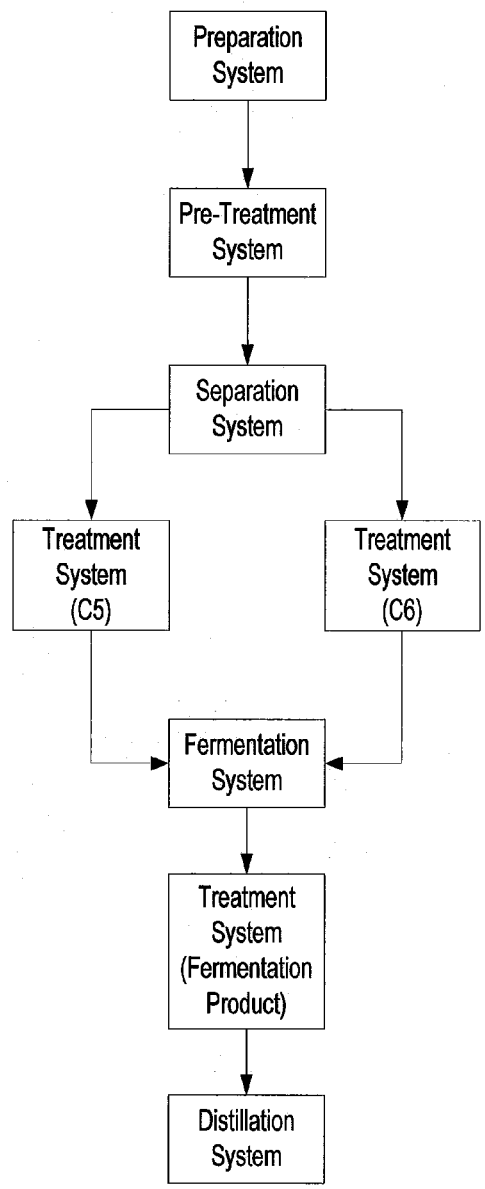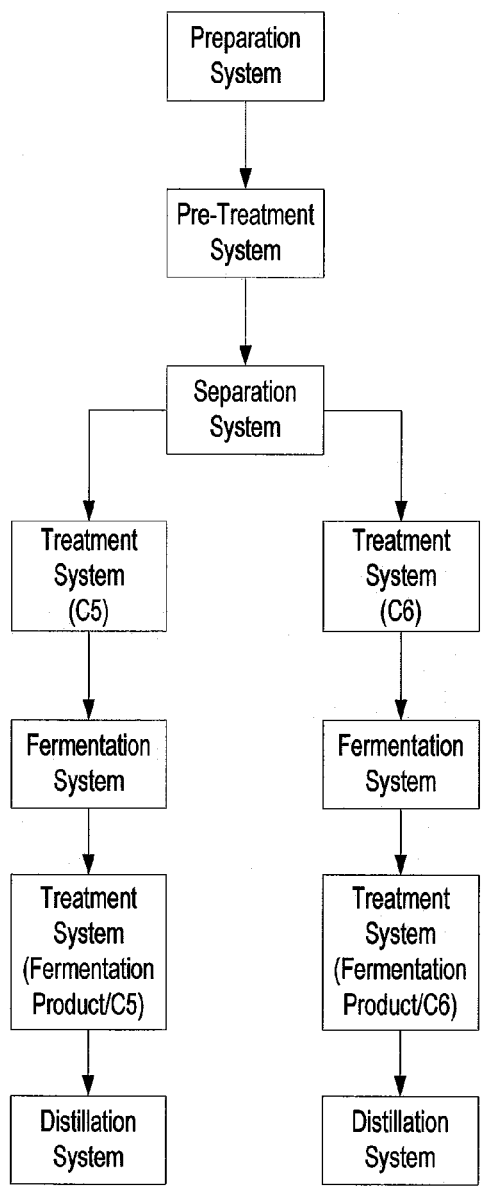
FIG. 5A                    FIG. 5B

SYSTEM FOR MANAGEMENT OF YEAST TO FACILITATE THE PRODUCTION OF ETHANOL

CROSS-REFERENCE TO RELATED APPLICATIONS

The present application claims priority to and incorporates by reference each of the following applications: U.S. Provisional Application Ser. No. 61/157,151, titled Propagation of Pentose Metabolizing Yeast Cells, filed on Mar. 3, 2009.

The present application is related to and incorporates by reference the following applications: (a) U.S. application Ser. No. 12/716,984, titled System for Pre-Treatment of Biomass for the Production of Ethanol, filed on Mar. 3, 2010; and (b) U.S. application Ser. No. 12/717,015, titled System for Fermentation of Biomass for the Production of Ethanol, filed Mar. 3, 2010.

FIELD

The present invention relates to a system for the production of cellulosic ethanol and recovery of other bioproducts. The present invention also relates to a system for management of yeast to facilitate the production of ethanol. The present invention further relates to a method of propagating ethanologen for use in the production of a fermentation product from biomass.

BACKGROUND

Ethanol can be produced from grain-based feedstocks (e.g. corn, sorghum/milo, barley, wheat, soybeans, etc.), from sugar (e.g. from sugar cane, sugar beets, etc.), and from biomass (e.g. from lignocellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter (grown for processing into bioproducts or for other purposes). In order to be used or processed, biomass will be harvested and collected from the field and transported to the location where it is to be used or processed.

In a conventional ethanol plant producing ethanol from corn, ethanol is produced from starch. Corn kernels are cleaned and milled to prepare starch-containing material for processing. (Corn kernels can also be fractionated to separate the starch-containing material (e.g. endosperm) from other matter (such as fiber and germ).) The starch-containing material is slurried with water and liquefied to facilitate saccharification where the starch is converted into sugar (e.g. glucose) and fermentation where the sugar is converted by an ethanologen (e.g. yeast) into ethanol. The product of fermentation (i.e. fermentation product) is beer, which comprises a liquid component containing ethanol and water and soluble components, and a solids component containing unfermented particulate matter (among other things). The fermentation product is sent to a distillation system. In the distillation system, the fermentation product is distilled and dehydrated into ethanol. The residual matter (e.g. whole stillage) comprises water, soluble components, oil and unfermented solids (i.e. the solids component of the beer with substantially all ethanol removed that can be dried into dried distillers grains (DDG) and sold as an animal feed product). Other co-products, for example syrup (and oil contained in the syrup), can also be recovered from the stillage. Water removed from the fermentation product in distillation can be treated for re-use at the plant.

In a biorefinery configured to produce ethanol from biomass, ethanol is produced from lignocellulosic material. Lignocellulosic biomass typically comprises cellulose, hemicellulose and lignin. Cellulose (a type of glucan) is a polysaccharide comprising hexose (C6) sugar monomers such as glucose linked in linear chains. Hemicellulose is a branched chain polysaccharide that may comprise several different pentose (C5) sugar monomers (such as xylose and arabinose) and small amounts of hexose (C6) sugar monomers in branched chains.

The biomass is prepared so that sugars in the lignocellulosic material (such as glucose from the cellulose and xylose from the hemicellulose) can be made accessible and fermented into a fermentation product from which ethanol can be recovered. After fermentation the fermentation product is sent to the distillation system, where the ethanol is recovered by distillation and dehydration. Other bioproducts such as lignin and organic acids may also be recovered as by-products or co-products during the processing of biomass into ethanol. Determination of how to more efficiently prepare and treat the biomass for production into ethanol will depend upon the source and type or composition of the biomass. Biomass of different types or from different sources is likely to vary in properties and composition (e.g. relative amounts of cellulose, hemicellulose, lignin and other components). For example the composition of wood chips will differ from the composition of corn cobs or switchgrass.

It would be advantageous to provide for a system for the production of cellulosic ethanol. It would also be advantageous to provide a system for management of yeast to facilitate the production of ethanol. It would further be advantageous to provide for a system that provides one or more features to facilitate improvement in the efficiency and yield of cellulosic ethanol from biomass.

SUMMARY

The present invention relates to a method of propagating ethanologen for use in the production of a fermentation product from biomass. The method comprises the steps of providing a medium for propagation of ethanologen; supplying a first cell mass of ethanologen to the medium; supplying xylose to the medium as a carbon source for the ethanologen; and maintaining the medium comprising the first cell mass of ethanologen at a pH of between about 5.0 and 6.0 and at a temperature of between about 26 and about 37 degrees Celsius so that the first cell mass of ethanologen is propagated into a second cell mass of ethanologen. The second cell mass of ethanologen is larger than the first cell mass of ethanologen.

The present invention also relates to a method of propagating ethanologen for use in the production of a fermentation product from biomass. The method comprises the steps of providing a medium for propagation of ethanologen; supplying a first cell mass of ethanologen to the medium; providing an agent to the medium; providing a component obtained from the biomass to the medium as a carbon source for the ethanologen; and maintaining the medium comprising the first cell mass of ethanologen at a pH of between about 5.0 and 6.0 and at a temperature of between about 26 and about 37 degrees Celsius so that the first cell mass of ethanologen is propagated into a second cell mass of ethanologen. The second cell mass of ethanologen is larger than the cell mass of the first amount of ethanologen. The biomass comprises lignocellulosic material; the lignocellulosic material comprises at least one of corn cobs, corn plant husks, corn plant leaves and corn plant stalks. The component is obtained from the lignocellulosic material; the component comprises pentose. Pentose comprises the carbon source for the ethanologen. The ethanologen comprises yeast cells capable of fermenting pentose into ethanol.

The present invention further relates to a system for propagating ethanologen for use in the production of a fermentation product from biomass in a fermentation system. The system comprises a first stage comprising a first vessel configured to maintain a medium comprising ethanologen; a second stage comprising a second vessel configured to maintain a medium supplied from the first stage; a source of xylose to be provided to the medium as a carbon source for ethanologen in the first stage; and a source of xylose to be provided to the medium as a carbon source for the ethanologen in the second stage. The ethanologen has a first cell mass when supplied to the first stage and the ethanologen has a second cell mass when supplied from the first stage to the second stage and the ethanologen has a third cell mass when supplied from the second stage. The medium in the first vessel is maintained at a pH of between about 5.0 and 6.0 and at a temperature of between about 26 and about 37 degrees Celsius so that ethanologen can be propagated into the second cell mass; the medium in the second vessel is maintained at a pH of between about 5.0 and 6.0 and at a temperature of between about 26 and about 37 degrees Celsius so that ethanologen can be propagated into the third cell mass. The second cell mass is at least 200 times larger than the first cell mass. The third cell mass is at least 20 times larger than the second cell mass.

BRIEF DESCRIPTION OF THE FIGURES AND TABLES

FIGS. 4A, 4B and 4C are schematic block diagrams of systems for treatment and processing of components from the production of ethanol from biomass.

FIGS. 5A and 5B are schematic diagrams of the process flow for systems for the production of ethanol from biomass.

TABLES 1A and 1B list the composition of biomass comprising lignocellulosic plant material from the corn plant according to exemplary and representative embodiments.

TABLES 2A and 2B list the composition of the liquid component of pre-treated biomass according to exemplary and representative embodiments.

TABLES 3A and 3B list the composition of the solids component of pre-treated biomass according to exemplary and representative embodiments.

TABLE 4 lists the growth medium composition according to Examples 1A through Example 4.

TABLES 5A and 5B list the results of use of a system according to Example 1A.

TABLES 6A and 6B list the results of use of a system according to Example 1B.

TABLES 7A, 7B and 7C list the results of use of a system according to Example 2.

TABLES 8A and 8B list the results of use of a system according to Example 3.

TABLES 9A and 9B list the results of use of a system according to Example 4.

TABLES 10A and 10B list the results of use of a system according to Example 5.

TABLES 11A through 11C list the results of use of a system according to Example 6.

DETAILED DESCRIPTION

Figure 1A:
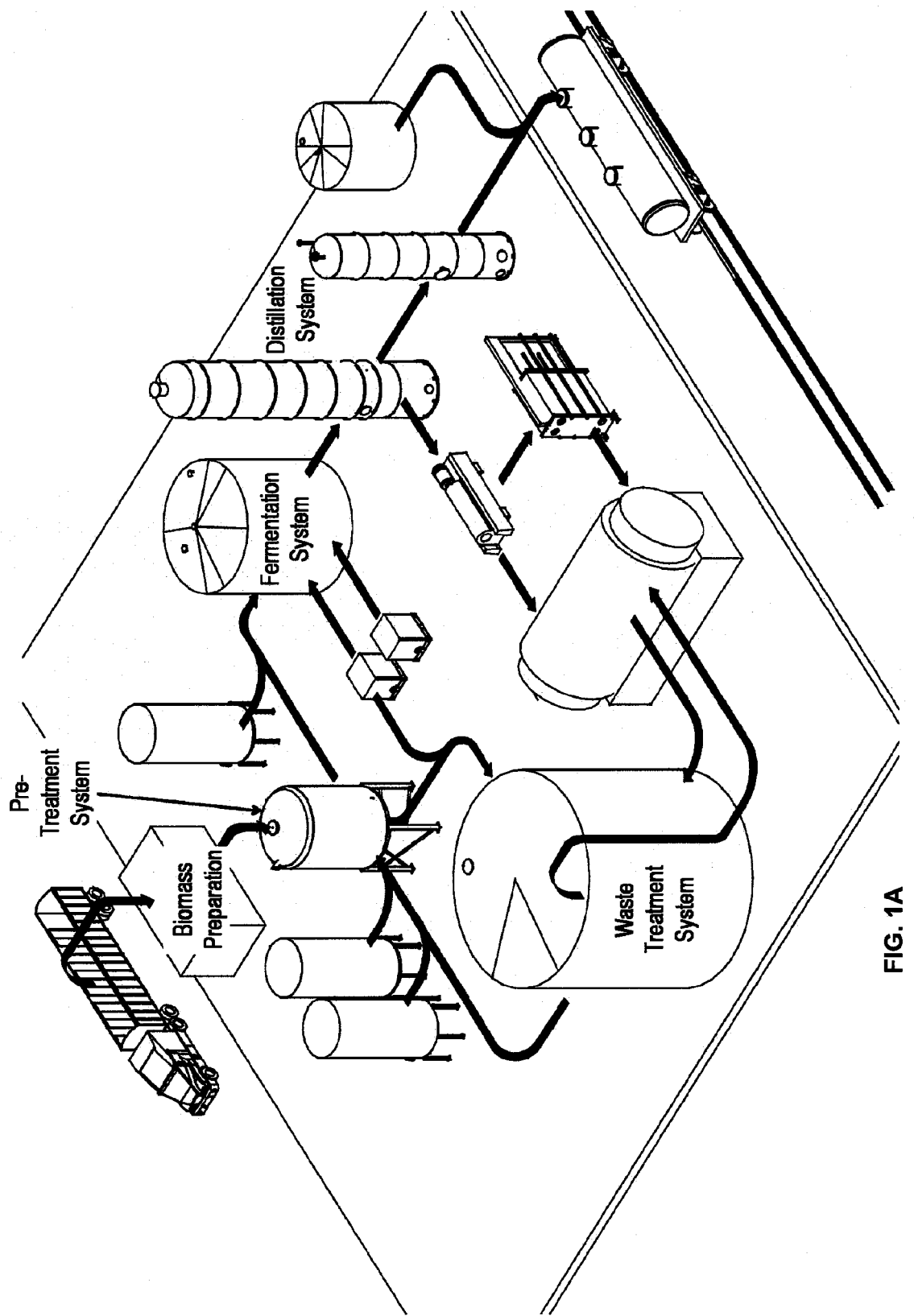
FIG. 1A is a perspective view of a biorefinery comprising a cellulosic ethanol production facility.

Referring to FIG. 1A, a biorefinery configured to produce ethanol from biomass is shown.

According to an exemplary embodiment, the biorefinery is configured to produce ethanol from biomass in the form of a lignocellulosic feedstock such as plant material from the corn plant (e.g. corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1A, the biorefinery comprises an area where biomass is delivered and prepared to be supplied to the cellulosic ethanol production facility. The cellulosic ethanol production facility comprises apparatus for preparation, pretreatment and treatment of the biomass into treated biomass suitable for fermentation into fermentation product in a fermentation system. The facility comprises a distillation system in which the fermentation product is distilled and dehydrated into ethanol. As shown in FIG. 1A, the biorefinery may also comprise a waste treatment system (shown as comprising an anaerobic digester and a generator). According to other alternative embodiments, the waste treatment system may comprise other equipment configured to treat, process and recover components from the cellulosic ethanol production process, such as a solid/waste fuel boiler, anaerobic digester, aerobic digester or other biochemical or chemical reactors.

Figure 1B:
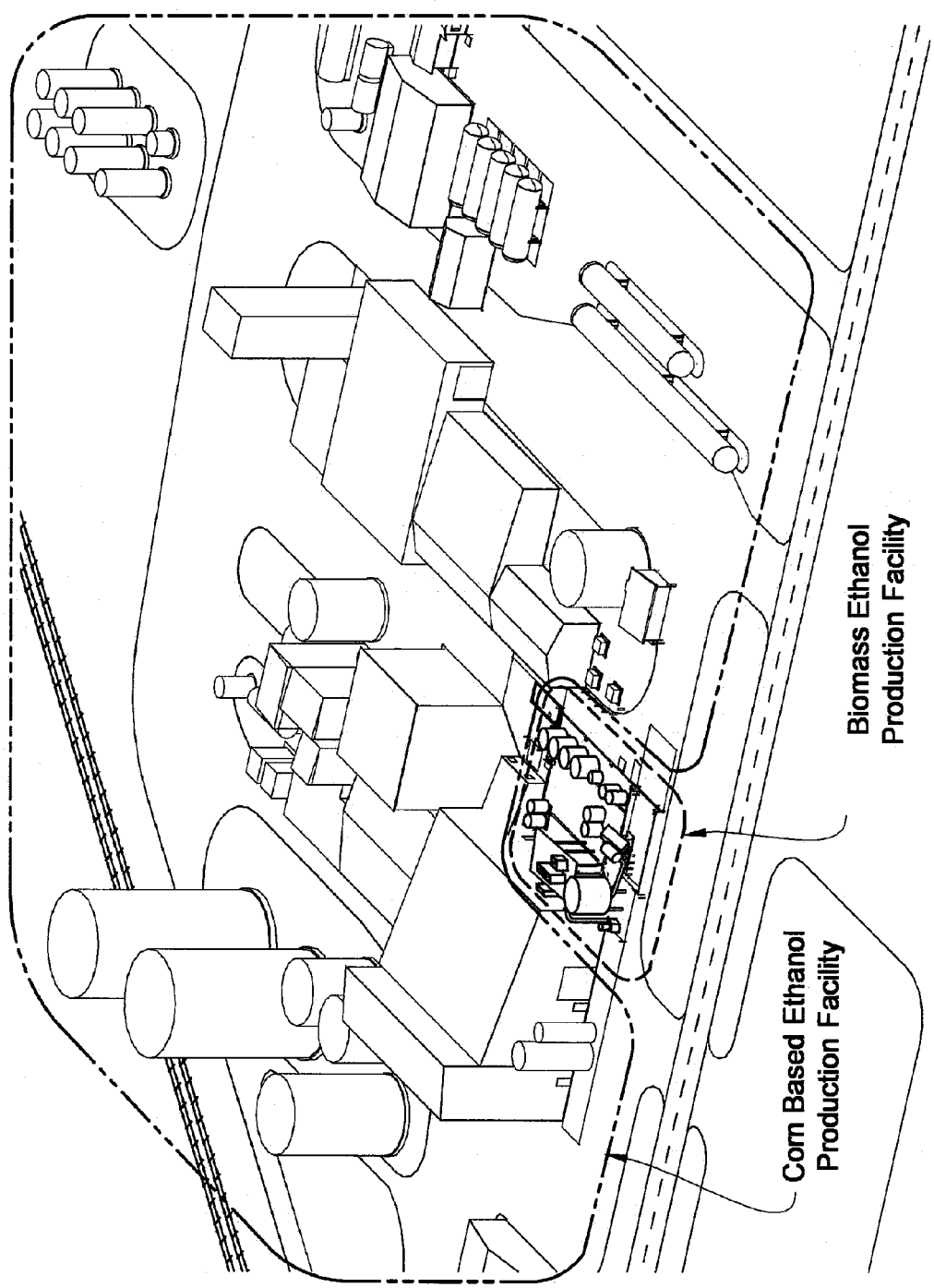
FIG. 1B is a perspective view of a biorefinery comprising a cellulosic ethanol production facility and a corn-based ethanol production facility.

As shown in FIG. 1B, according to an exemplary embodiment, a biorefinery may comprise a cellulosic ethanol production facility (which produces ethanol from lignocellulosic material and components of the corn plant) co-located with a corn-based ethanol production facility (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant or a facility that processes agricultural products.

Figure 2:
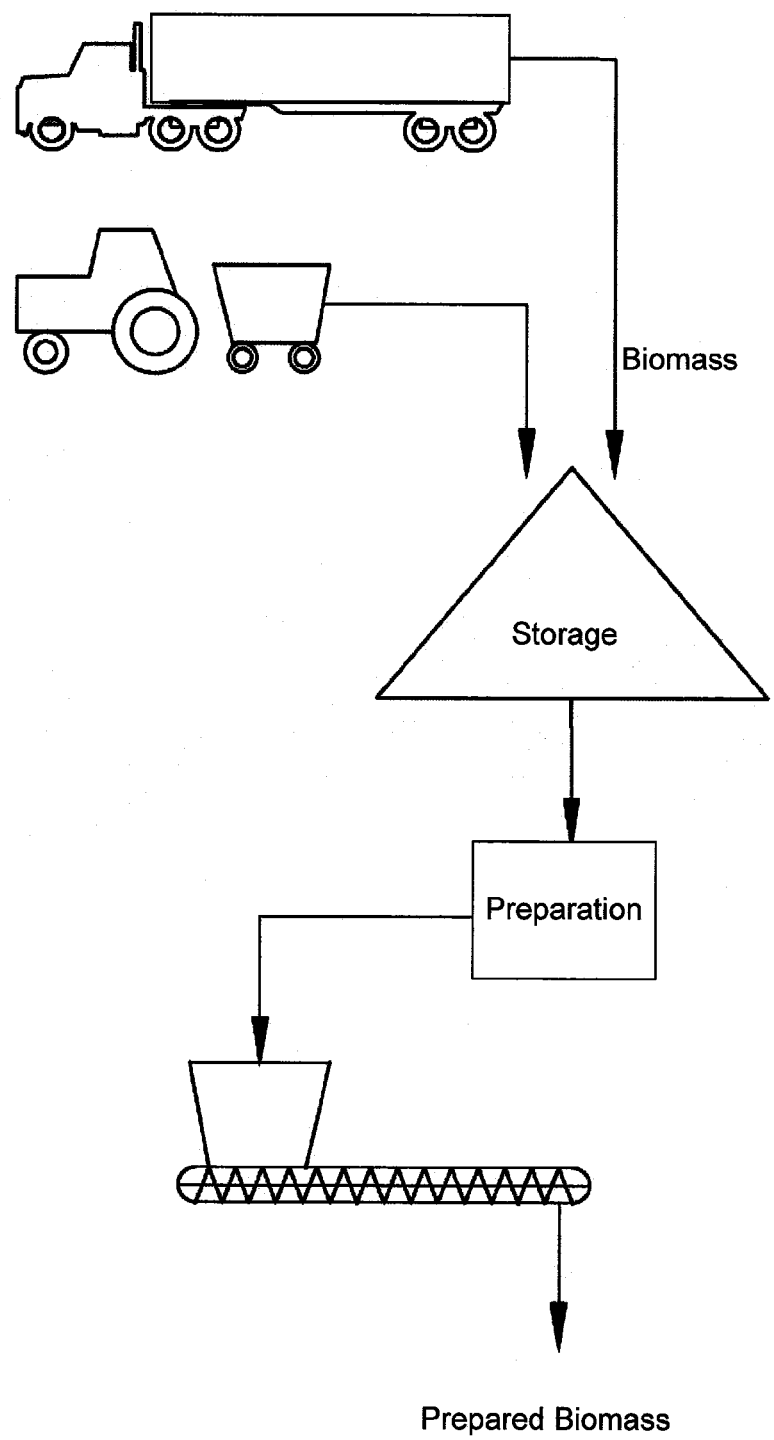
FIG. 2 is a schematic diagram of a system for receipt and preparation of biomass for a cellulosic ethanol production facility.

Referring to FIG. 2, a system for preparation of biomass delivered to the biorefinery is shown. The biomass preparation system may comprise apparatus for receipt/unloading of the biomass, cleaning (i.e. removal of foreign matter), grinding (i.e. milling, reduction or densification), and transport and conveyance for processing at the plant. According to an exemplary embodiment, biomass in the form of corn cobs and stover may be delivered to the biorefinery and stored (e.g. in bales, piles or bins, etc.) and managed for use at the facility. According to a preferred embodiment, the biomass may comprise at least 20 to 30 percent corn cobs (by weight) with corn stover and other matter. According to other exemplary embodiments, the preparation system of the biorefinery may be configured to prepare any of a wide variety of types of biomass (i.e. plant material) for treatment and processing into ethanol and other bioproducts at the plant.

Figure 3:
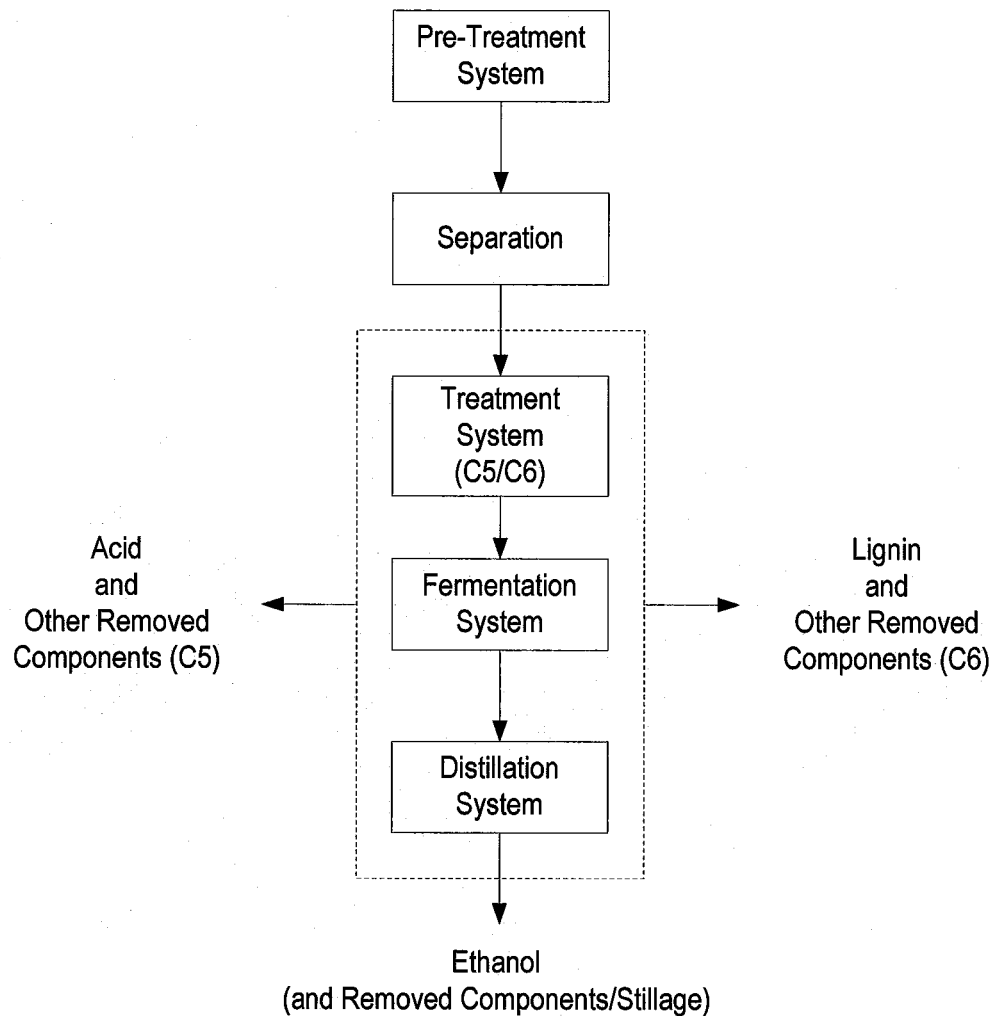
FIG. 3 is a schematic block diagram of a system for the production of ethanol from biomass.

Referring to FIG. 3, a schematic diagram of the cellulosic ethanol production facility is shown. According to a preferred embodiment, biomass comprising plant material from the corn plant is prepared and cleaned at a preparation system. After preparation, the biomass is mixed with water into a slurry and is pre-treated at a pre-treatment system. In the pre-treatment system, the biomass is broken down (e.g. by hydrolysis) to facilitate separation into a liquid component (e.g. a stream comprising the C5 sugars) and a solids component (e.g. a stream comprising cellulose from which the C6 sugars can be made available). The C5-sugar-containing liquid component (C5 stream) and C6-sugar-containing solids component (C6 stream) can be treated (as may be suitable) and fermented in a fermentation system. Fermentation product from the fermentation system is supplied to a distillation system where the ethanol is recovered.

As shown in FIGS. 3 and 4A, removed components from treatment of the C5 stream can be treated or processed to recover by-products, such as organic acids and furfural. As shown in FIGS. 3 and 4B, removed components from treatment of the C6 stream, such as lignin or other components, can be treated or processed into bioproducts or into fuel (such as lignin for a solid fuel boiler or methane produced by treatment of residual/removed matter such as acids and lignin in an anaerobic digester). As shown in FIGS. 4A, 4B and 4C, components removed during treatment and production of ethanol from the biomass from either or both the C5 stream and the C6 stream (or at distillation) may be processed into bioproducts (e.g. by-products or co-products) or recovered for use or reuse. As shown in FIG. 4C, removed components from the distillation system (such as stillage or removed solids) or from the treatment of the fermentation product before distillation (e.g. removed solids and particulate matter, which may comprise residual lignin, etc.) can be treated or processed into bioproducts or fuel (e.g. methane produced in an anerobic digester).

According to a preferred embodiment, the biomass comprises plant material from the corn plant, such as corn cobs, husks and leaves and stalks; the composition of the plant material (i.e. cellulose, hemicellulose and lignin) will be approximately as indicated in TABLES 1A and 1B. According to a preferred embodiment, the plant material comprises corn cobs, husks/leaves and stalks (i.e. after cleaning/removal of foreign matter); for example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any other combinations of cobs, husks/leaves and stalks from the corn plant. See TABLE 1A. According to an exemplary embodiment, corn stalks comprise the upper half or three-quarters portion of the stalk. According to an alternative embodiment, the lignocellulosic plant material may comprise fiber from the corn kernel (e.g. in some combination with other plant material). TABLE 1B provides typical and expected ranges believed to be representative of the composition of biomass comprising lignocellulosic material from the corn plant. According to exemplary embodiments, the lignocellulosic plant material of the biomass (from the corn plant) will comprise (by weight) cellulose at about 30 to 55 percent, hemicellulose at about 20 to 50 percent, and lignin at about 10 to 25 percent; according to a particularly preferred embodiment, the lignocellulosic plant material of the biomass (cobs, husks/leaves and stalk portions from the corn plant) will comprise (by weight) cellulose at about 35 to 45 percent, hemicellulose at about 24 to 42 percent, and lignin at about 12 to 20 percent. According to a particularly preferred embodiment, pre-treatment of the biomass will yield a liquid component that comprises (by weight) xylose at no less than 1.0 percent and a solids component that comprises (by weight) cellulose (from which glucose can be made available) at no less than 45 percent.

Referring to FIGS. 5A and 5B, exemplary embodiments of systems for the production of ethanol from biomass are shown. As shown in FIGS. 5A and 5B, biomass is pre-treated in a pre-treatment system and then separated into a liquid component and a solids component.

According to a preferred embodiment, in the pre-treatment system an acid will be applied to the prepared biomass to facilitate the break down of the biomass for separation into the liquid component (C5 stream from which fermentable C5 sugars can be recovered) and the solids component (C6 stream from which fermentable C6 sugars can be accessed). According to a preferred embodiment, the acid can be applied to the biomass in a reaction vessel under determined operating conditions (i.e. acid concentration, pH, temperature, time, pressure, solids loading, flow rate, supply of process water or steam, etc.) and the biomass can be agitated/mixed in the reaction vessel to facilitate the break down of the biomass. According to exemplary embodiments, an acid such as sulfuric acid, hydrochloric acid, nitric acid, phosphoric acid, acetic acid, etc. (or a formulation/mixture of acids) can be applied to the biomass. According to a particularly preferred embodiment, sulfuric acid will be applied to the biomass in pre-treatment.

The liquid component (C5 stream) comprises water, dissolved sugars (such as xylose, arabinose and glucose) to be made available for fermentation into ethanol, acids and other soluble components recovered from the hemicellulose. (TABLE 2B provides typical and expected ranges believed to be representative of the composition of biomass comprising lignocellulosic material from the corn plant.) According to an exemplary embodiment, the liquid component may comprise approximately 5 to 7 percent solids (i.e. suspended/residual solids such as partially-hydrolyzed hemicellulose, cellulose and lignin). According to a particularly preferred embodiment, the liquid component will comprise at least 2 to 4 percent xylose (by weight); according to other exemplary embodiments, the liquid component will comprise no less than 1 to 2 percent xylose (by weight). TABLES 2A and 2B list the composition of the liquid component of pre-treated biomass (from prepared biomass as indicated in TABLES 1A and 1B) according to exemplary and representative embodiments.

The solids component (C6 stream) comprises water, acids and solids such as cellulose from which sugar, such as glucose, can be made available for fermentation into ethanol, and lignin. (TABLE 3B provides typical and expected ranges believed to be representative of the composition of biomass comprising lignocellulosic material from the corn plant.) According to an exemplary embodiment, the solids component may comprise approximately 10 to 40 percent solids (by weight) (after separation); according to a particularly preferred embodiment, the solids component will comprise approximately 20 to 30 percent solids (by weight). According to a preferred embodiment, the solids in the solids component comprise no less than 30 percent cellulose and the solids component may also comprise other dissolved sugars (e.g. glucose and xylose). TABLES 3A and 3B list the composition of the solids component of pre-treated biomass (from prepared biomass as indicated in TABLES 1A and 1B) according to exemplary and representative embodiments.

During pre-treatment, the severity of operating conditions (such as pH, temperature and time) may cause formation of components that are inhibitory to fermentation. For example, under some conditions, the dehydration of C5 sugars (such as xylose or arabinose) may cause the formation of furfural and/or hydroxymethylfurfural (HMF). Acetic acid may also be formed, for example when acetate is released during the break down of cellulose in pre-treatment. Sulfuric acid, which may be added to prepared biomass to facilitate pre-treatment, if not removed or neutralized, may also be inhibitory to fermentation. According to an exemplary embodiment, by adjusting pre-treatment conditions (such as pH, temperature and time), the formation of inhibitors can be reduced or managed; according to other exemplary embodiments, components of the pre-treated biomass may be given further treatment to remove or reduce the level of inhibitors (or other undesirable matter).

Referring to FIGS. 5A and 5B, after pre-treatment and separation the C5 stream and the C6 stream are processed separately; as shown, the C5 stream and the C6 stream may be processed separately prior to co-fermentation (C5/C6 fermentation as shown in FIG. 5A) or processed separately including separate fermentation (separate C5 fermentation and C6 fermentation as shown in FIG. 5B).

Treatment of the C5 stream (liquid component) of the biomass may be performed in an effort to remove components that are inhibitory to efficient fermentation (e.g. furfural, HMF, sulfuric acid and acetic acid) and residual lignin (or other matter) that may not be fermentable from the C5 sugar component so that the sugars (e.g. xylose, arabinose, as well as other sugars such as glucose) are available for fermentation. The C5 sugars in the C5 stream may also be concentrated to improve the efficiency of fermentation (e.g. to improve the titer of ethanol for distillation).

Treatment of the C6 stream (solids component) of the biomass may be performed to make the C6 sugars available for fermentation. According to a preferred embodiment, hydrolysis (such as enzyme hydrolysis) may be performed to access the C6 sugars in the cellulose; treatment may also be performed in an effort to remove lignin and other non-fermentable components in the C6 stream (or to remove components such as residual acid or acids that may be inhibitory to efficient fermentation).

According to an exemplary embodiment shown in FIG. 5A, after pre-treatment and separation the C5 stream and the C6 stream can be treated separately and subsequently combined after treatment (e.g. as a slurry) for co-fermentation in the fermentation system to produce a C5/C6 fermentation product from the available sugars (e.g. xylose and glucose); the C5/C6 fermentation product can (after treatment, if any) be supplied to the distillation system for recovery of the ethanol (e.g. through distillation and dehydration). According to an exemplary embodiment shown in FIG. 5B, the C5 stream and the C6 stream can each be separately processed through fermentation and distillation (after treatment, if any) to produce ethanol. According to any preferred embodiment, a suitable fermenting organism (ethanologen) will be used in the fermentation system; the selection of an ethanologen may be based on various considerations, such as the predominant types of sugars present in the slurry. Dehydration and/or denaturing of the ethanol produced from the C5 stream and the C6 stream may be performed either separately or in combination.

Figure 6A:
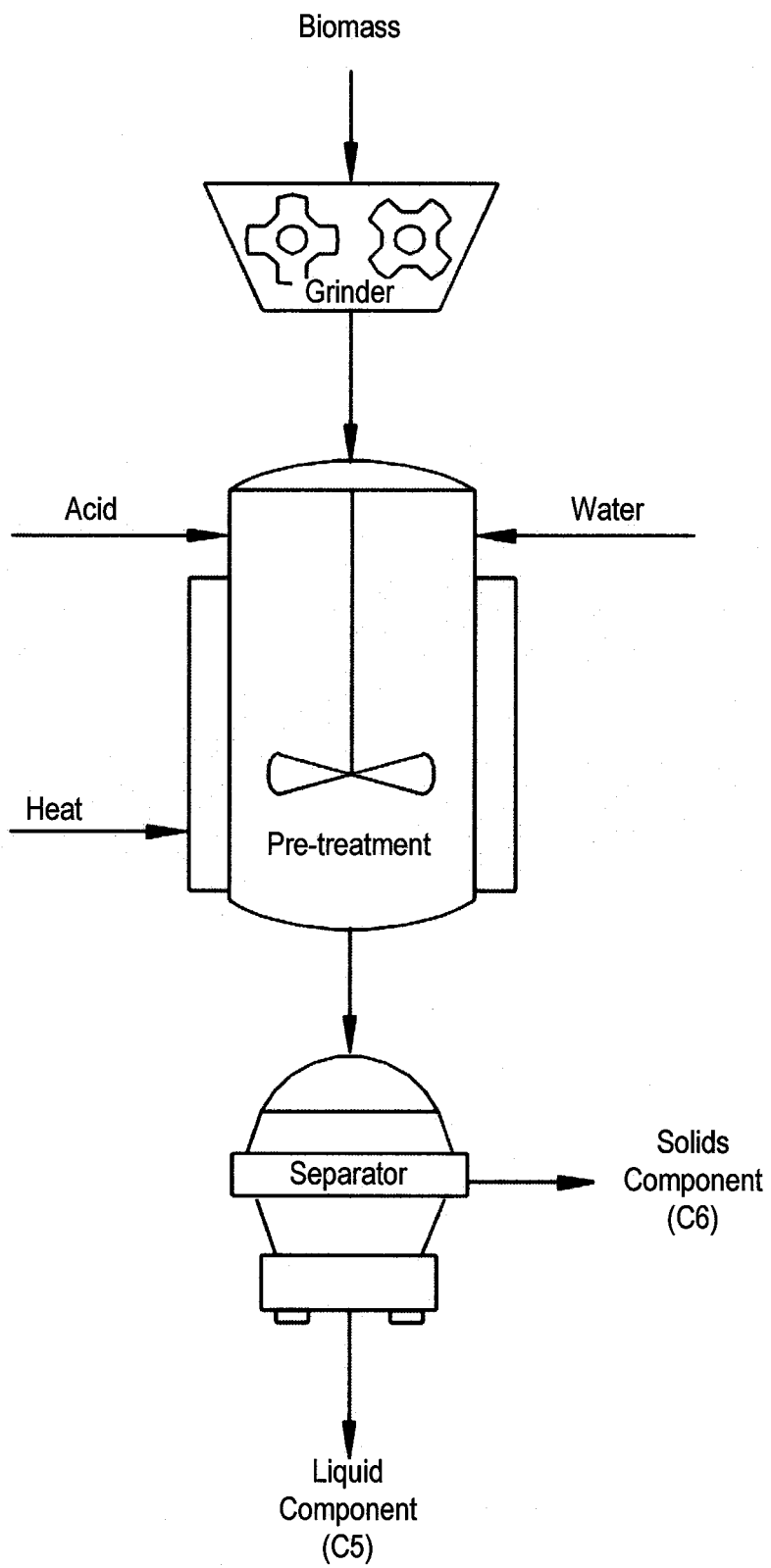
FIG. 6A is a schematic block diagram of apparatus used for preparation, pre-treatment and separation of biomass.
Figure 6B:
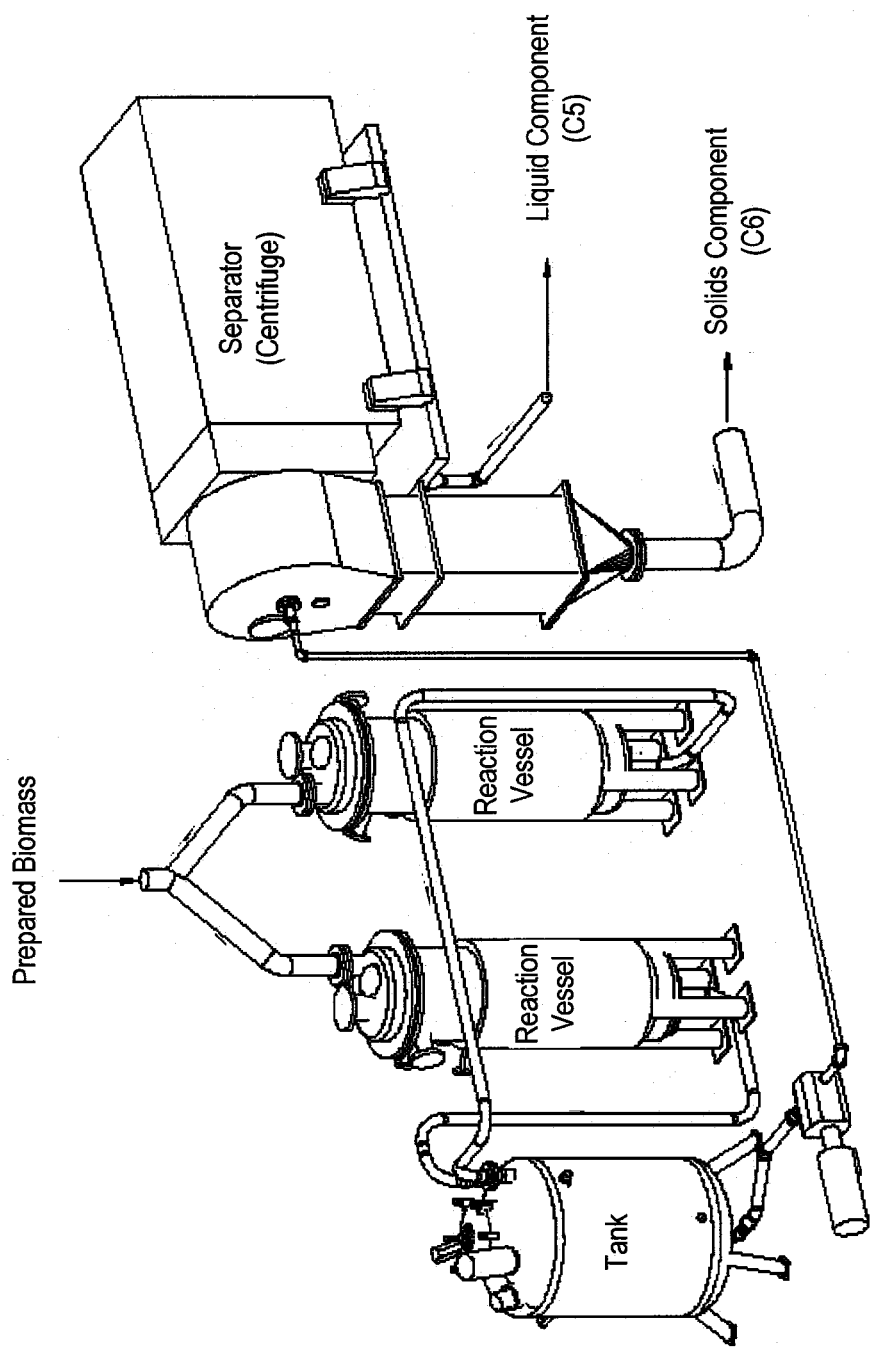
FIG. 6B is a perspective view of apparatus used to pre-treat and separate the biomass.

FIGS. 6A and 6B show the apparatus used for preparation, pre-treatment and separation of lignocellulosic biomass according to an exemplary embodiment. As shown, biomass is prepared in a grinder (e.g. grinder or other suitable apparatus or mill). Pre-treatment of the prepared biomass is performed in a reaction vessel (or set of reaction vessels) supplied with prepared biomass and acid/water in a predetermined concentration (or pH) and other operating conditions. As shown in FIG. 6B, the pre-treated biomass can be separated in a centrifuge into a liquid component (C5 stream comprising primarily liquids with some solids) and a solids component (C6 stream comprising liquids and solids such as lignin and cellulose from which glucose can be made available by further treatment).

Figure 7A:
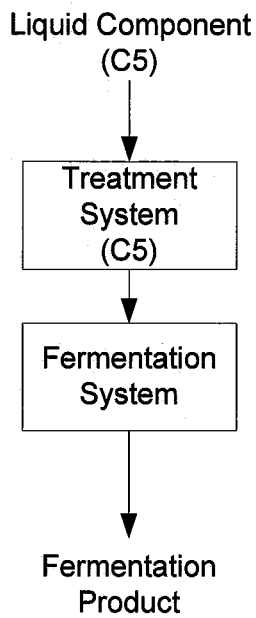
FIG. 7A is a schematic block diagram of the process flow for a system for the production of a fermentation product from a liquid component (C5).
Figure 7B:
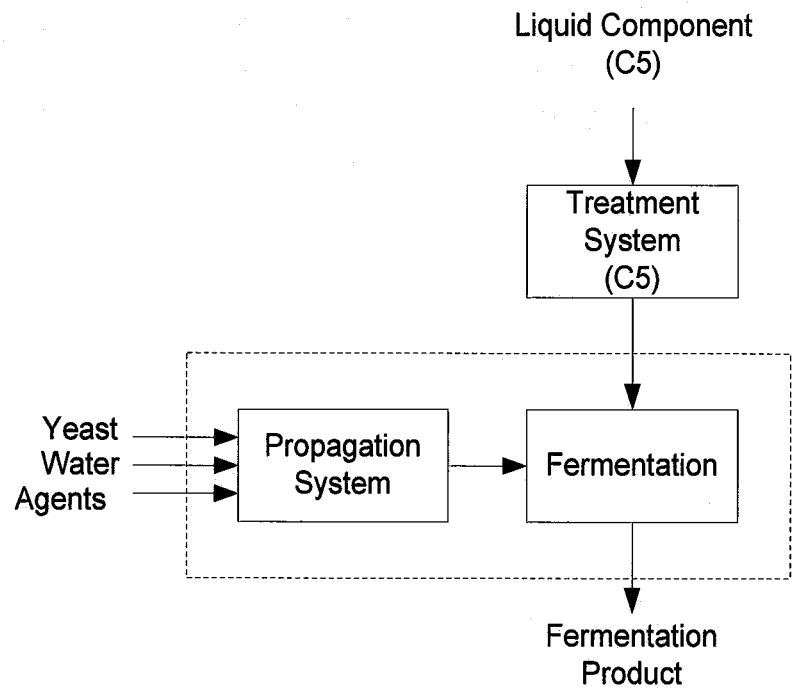
FIG. 7B is a schematic block diagram of the process flow of a system according to an exemplary embodiment.

As shown in FIGS. 7A and 7B, a liquid component (C5 stream) is introduced to a treatment system. In the treatment system, the C5 stream may be treated by filtration and/or by concentration into a treated liquid component that comprises sugars available for fermentation. The treated liquid component is supplied to a fermentation system to produce by fermentation of the sugars with an ethanologen (i.e. an organism such as yeast) a fermentation product (that comprises ethanol).

According to a preferred embodiment, the ethanologen comprises a yeast derived from genetically modified recombinant *Saccharomyces cerevisiae*. According to a particularly preferred embodiment, the ethanologen is a strain of *Saccharomyces cerevisiae* yeast altered to convert xylose and glucose to ethanol (a genetically modified yeast derived from an organism as described in U.S. Pat. No. 7,622,284, assigned to Royal Nedalco B.V.).

Referring to FIG. 7B, a propagation system is provided for the ethanologen (shown as yeast). In the propagation system, yeast is supplied with a growth medium (e.g. water and a carbon source, such as sugar) and an agent (e.g. nutrients, etc.) to facilitate the growth of a sufficient amount of yeast (i.e. yeast cell mass) for inoculation (i.e. yeast inoculum to be supplied) to the fermentation system.

According to an exemplary embodiment the growth medium for the propagation system will comprise, for example, a sterile yeast extract-peptone medium, xylose as the carbon source, and other agents (e.g. nutrients). Agents supplied with the ethanologen may include antibiotics, supplemental or accessory enzymes, nutrients or other components providing nutritional or other benefits to the organism. Nutrients may comprise yeast extract, urea, diammonium phosphate, magnesium sulfate, zinc sulfate or other salts, etc. According to an exemplary embodiment, the yeast inoculum is incubated under conditions comprising a temperature of about 30 degrees Celsius and a pH of about 5.5 for about 17 hours. According to alternative embodiments, to grow (inoculate) the yeast in the propagation system the temperature may be maintained in a range of about 28 to 32 degrees Celsius and the pH in a range of about 5.2 to 5.8 for a time of at least 12 hours.

Figure 7C:
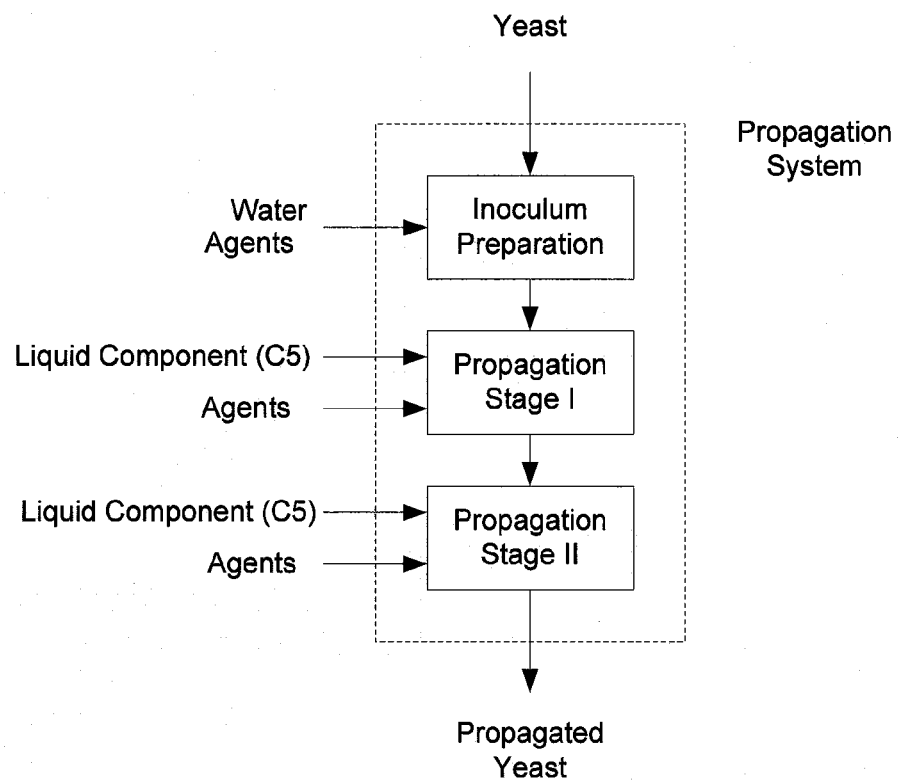
FIG. 7C is a schematic block diagram of the process flow of a system according to an exemplary embodiment.
Figure 9:
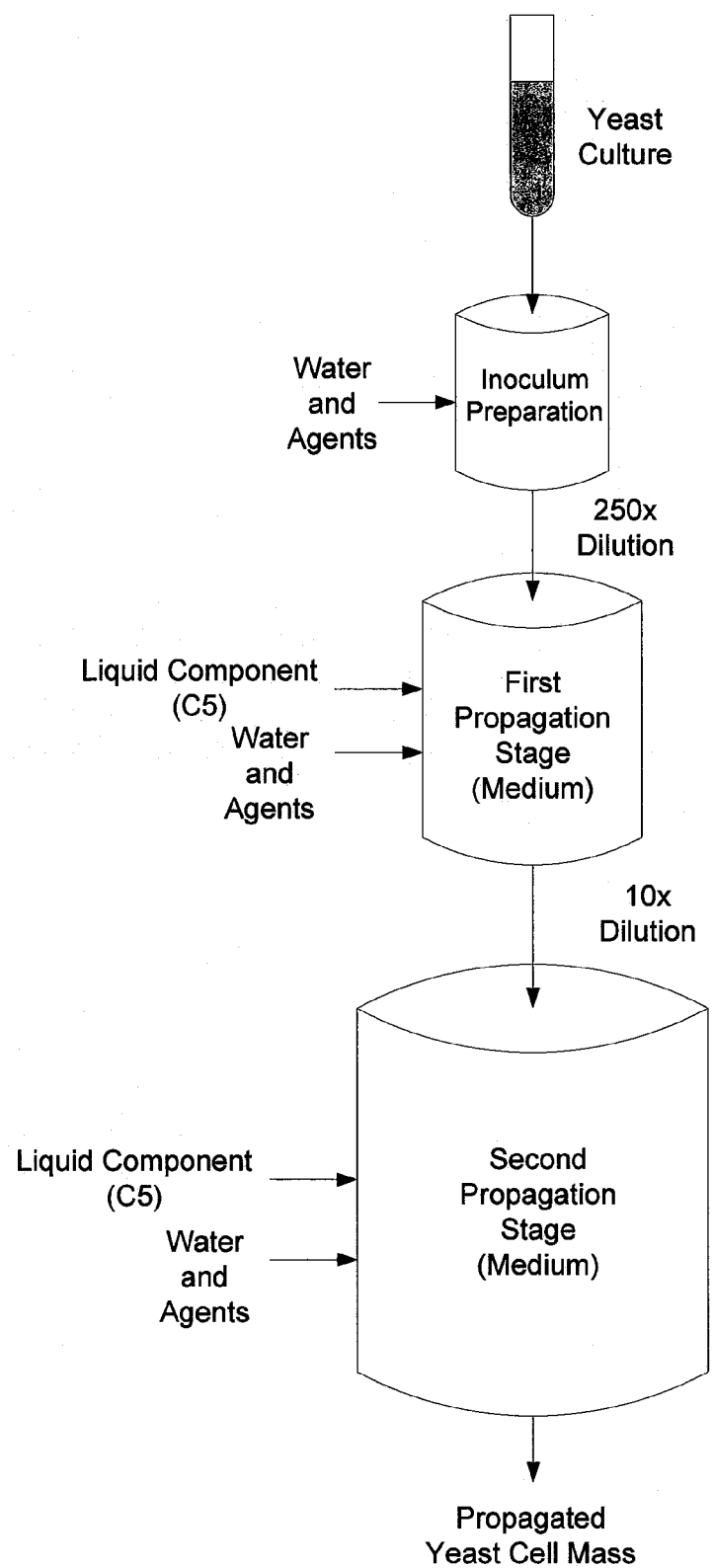
FIG. 9 is schematic diagram of a system according to an exemplary embodiment.

Referring to FIGS. 7C and 9, an exemplary embodiment of the propagation system for the ethanologen (shown as yeast) employing two stages is shown. As shown in FIG. 9, a yeast culture can be grown into an initial yeast inoculum that can be provided to the first stage of the propagation system.

In the first propagation stage, the initial yeast inoculum is transferred to a larger vessel and diluted (e.g. by 250×). In the vessel, the initial yeast inoculum and a portion of the C5 stream (i.e. liquid component comprising C5/other sugars) and water may be supplied along with agents (such as nutrients) and fresh yeast. According to a preferred embodiment, yeast is grown in the first propagation stage under conditions comprising a temperature of about 30 degrees Celsius and a pH of about 5.5 for about 24 hours. According to other exemplary embodiments, the temperature may be maintained in a range of about 26 to 37 degrees and the pH in a range of about 3.5 to 6.5 for a time of at least 24 hours. In the second propagation stage, the yeast inoculum from the first propagation stage is transferred to a larger vessel and diluted (e.g. by 10×). In the vessel, the yeast inoculum from the first propagation stage and a portion of the C5 stream (i.e. liquid component comprising C5/other sugars) and water may be supplied along with agents (such as nutrients) and fresh yeast. According to a preferred embodiment, yeast is grown in the second propagation stage under conditions comprising a temperature of about 30 degrees Celsius and a pH of about 5.5 for about 24 hours. According to other exemplary embodiments, the temperature may be maintained in a range of about 26 to 37 degrees and the pH in a range of about 3.5 to 6.5 for a time of at least 24 hours.

The fermentation product (which may also be referred to as beer or fermentation broth or as comprising beer or fermentation broth) will comprise ethanol and water as well as unfermented matter (e.g. any unfermented sugars) and non-fermentable matter (e.g. residual lignin and other solids). The fermentation product will also comprise in the form of particulate matter the ethanologen (i.e. yeast cells) that was used to produce ethanol as well as other components produced by the fermentation system, for example, such as glycerol (a product of fermentation) and acetic acid.

Figure 8A:
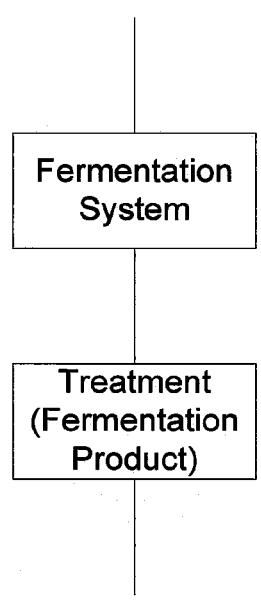
FIG. 8A is a schematic block diagram of the process flow of a system according to an exemplary embodiment.
Figure 8B:
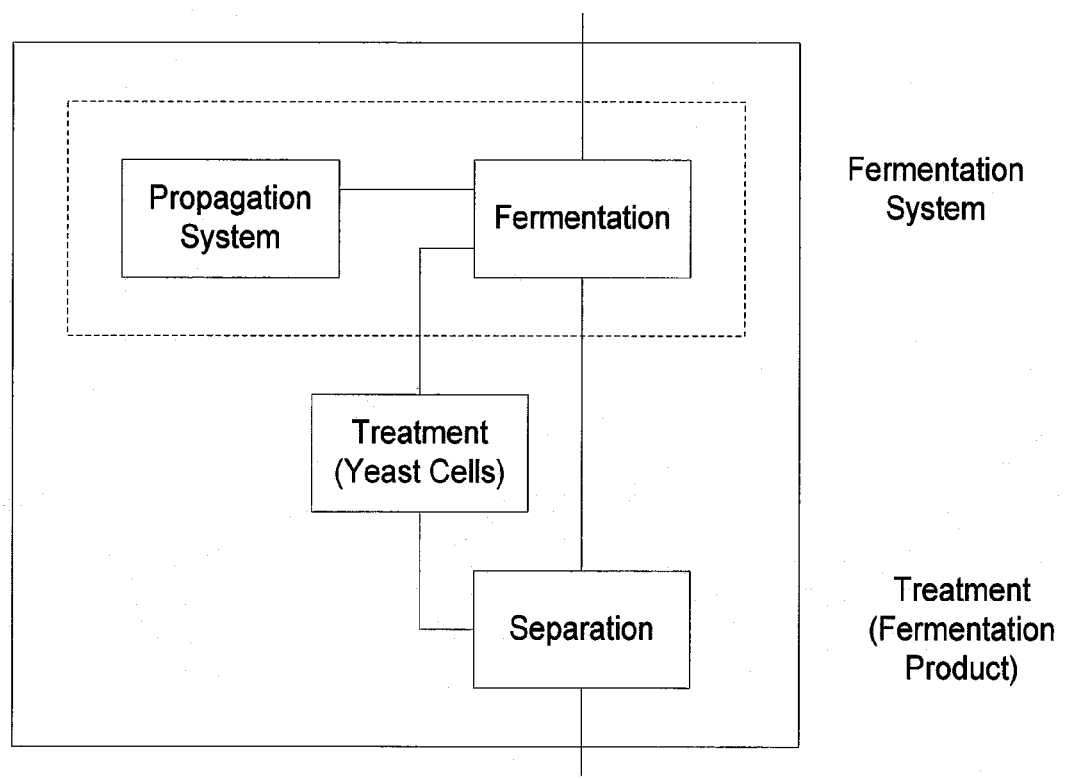
FIG. 8B is a schematic block diagram of the process flow of a system according to an exemplary embodiment.

As shown in FIGS. 8A and 8B, according to an exemplary embodiment, a treatment system for the fermentation product may also be provided. The treatment system can comprise separation of the fermentation product into a liquid component (i.e. a treated fermentation product, which will comprise substantially ethanol and water) and a solids component (which will comprise substantially solids matter such as the ethanologen/yeast cells). According to a preferred embodiment, as shown in FIG. 8B, the separation of the fermentation product into the liquid component and solids component can be performed on a centrifuge. As shown in FIG. 8B, the solids component from treatment comprising the yeast cells can be supplied to and re-used in the fermentation system (i.e. recycled for use in a fermentation tank) along with additional or fresh yeast cells (if necessary). The yeast cells may be treated in a yeast cell treatment system. The yeast cell treatment system may comprise washing the yeast cells and separating the yeast cells prior to recirculation to a fermentation tank or the fermentation product stream.

According to any preferred embodiment, the yeast propagation system will provide for the growth of yeast into a suitable yeast cell mass at a suitable rate to be supplied to the fermentation system. According to a preferred embodiment, the system will allow for the growth of yeast using xylose as a carbon source for growth. According to a particularly preferred embodiment, the system will allow for the selective growth of yeast that can use xylose as a carbon source (i.e. yeast that will propagate in a medium comprising xylose) even if other yeast is present (i.e. as a contaminant); in a medium that provides xylose as a sole carbon source (i.e. a medium that does not contain substantial amounts of glucose), yeast that are capable of propagating using xylose as a carbon source will propagate and other/contaminant yeast that may not be as capable of propagating using xylose as a carbon source (such as more common forms of yeast that typically propagate in a medium containing glucose) will not propagate at the same rate (or at all). According to a particularly preferred embodiment, the yeast will be capable of fermenting both xylose and glucose into ethanol. According to a preferred embodiment, the yeast propagation system will provide a growth medium and environment in which the yeast will convert sugar (e.g. xylose) into yeast cell mass rather than ethanol, for example, under conditions such as aeration (see FIGS. 15A and 15B) or will allow the yeast to withstand higher concentrations of sugar (e.g. xylose) during propagation (see FIGS. 16A and 16B). According to any preferred embodiment, the system will facilitate the efficient growth of yeast cell mass into an inoculum that can be provided to the fermentation system in a biorefinery. According to a particularly preferred embodiment the yeast cell mass will grow by about 200 to 500 fold in the first stage and about 20 to 40 fold in the second stage.

A series of Examples were conducted according to exemplary embodiments of the yeast propagation system (as shown, for example, in FIGS. 7B, 7C and 9) to evaluate ethanologen growth under various conditions. The ethanologen used in the Examples was a strain of *Saccharomyces cerevisiae* yeast able to convert xylose and glucose to ethanol (a genetically modified yeast derived from an organism as described in U.S. Pat. No. 7,622,284, by Royal Nedalco B.V., for example, Strain No. RWB218; Strain No. RN1001; and Strain No. RN1014). Data from the Examples is shown in FIGS. 10A through 16C and TABLES 5A through 11C. TABLE 4 lists the composition of the growth medium (including added agents such as nutrients) according to Examples 1A through 4.

An ethanologen culture was grown into an initial inoculum (yeast inoculum) using a sterile yeast extract-peptone (YP) medium (with 12.5 grams yeast extract per liter of medium and 10 grams peptone per liter). The inoculum was incubated at 30 degrees Celsius for approximately 17 to 18 hours. An inoculum to media ratio of 1:250 was used. A pump was used to control the xylose feed rate. The pH of the medium was able to be maintained at 5.5 (by adding a 45 percent by weight solution of potassium hydroxide). The samples were periodically analyzed for yeast growth (cell mass), sugars, organic acids and ethanol. The optical density was measured (at 600 nanometers using a spectrophotometer) as an indication of the amount (i.e. cell mass) of yeast in the sample. (HPLC was used to analyze other components.)

Example 1A

Figure 10A:
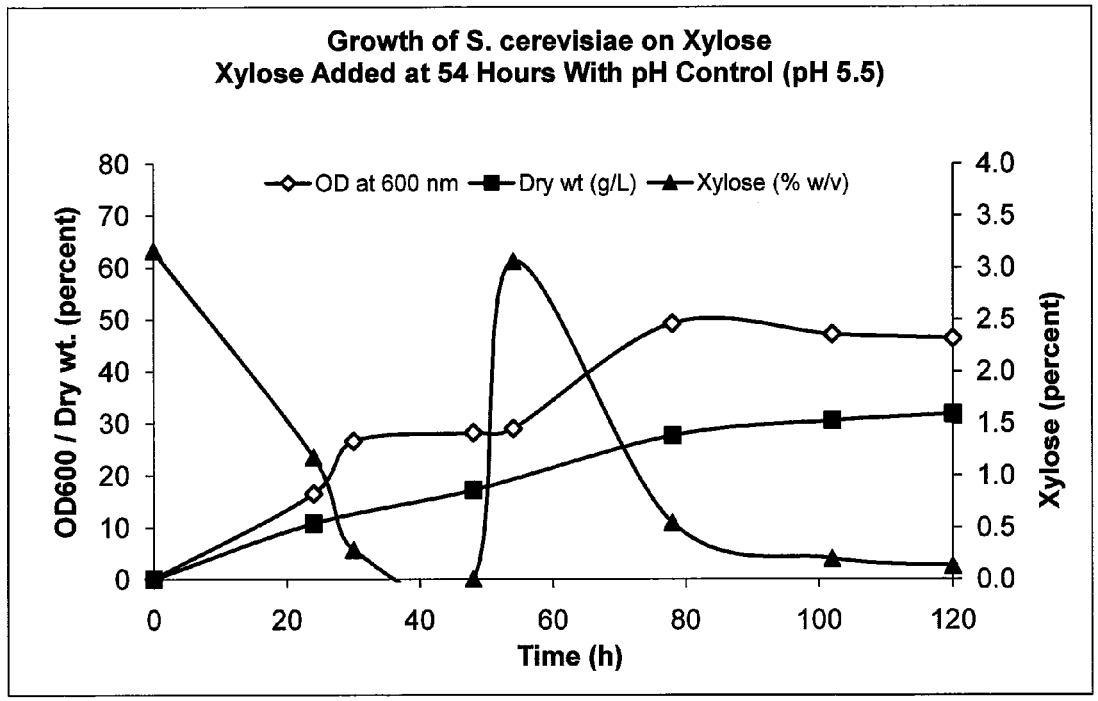
FIG. 10A is a line graph showing the growth of ethanologen using xylose.
Figure 10B:
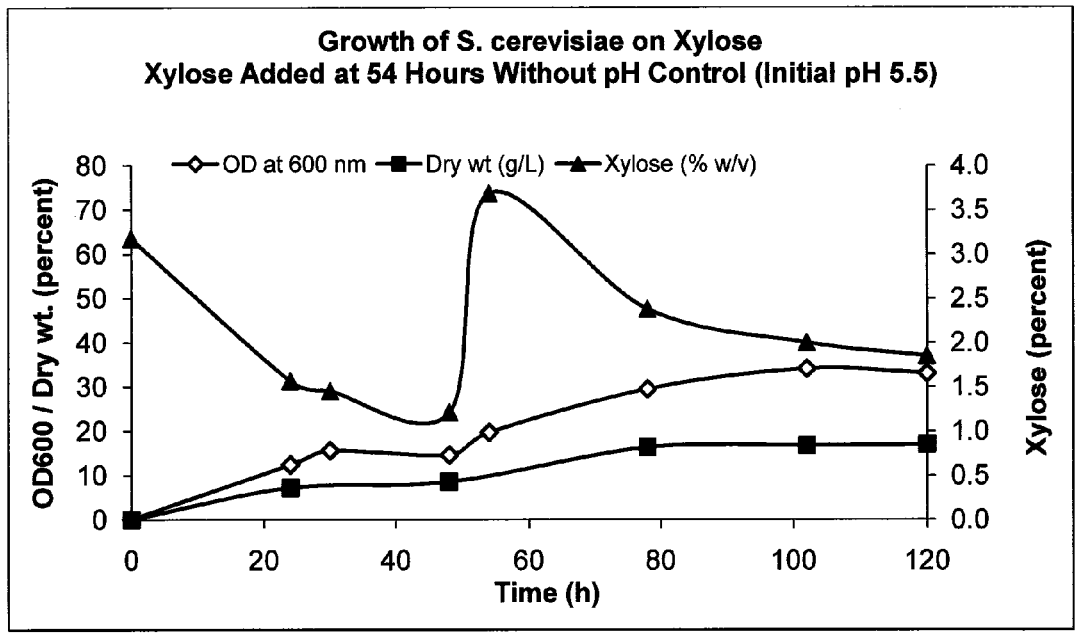
FIG. 10B is a line graph showing the growth of ethanologen using xylose.

The propagation system was used in Example 1A to evaluate the effect of pH regulation on the growth of the ethanologen. The ethanologen was yeast (Strain No. RN1001). Samples were prepared in two separate reaction vessels. The samples comprised a medium (e.g. water and agents, such as nutrients, as indicated in TABLE 4) and the yeast inoculum. The samples also comprised xylose at a concentration of 30 grams per liter (of medium). The pH of the samples in each reaction vessel was adjusted to 5.5. The temperature of each reaction vessel was held at 30 degrees Celsius. The yeast was propagated in each reaction vessel for 54 hours. In one of the reaction vessels, the pH was maintained (regulated) at 5.5; in the other reaction vessel the pH was unregulated. After 54 hours xylose solution (50 percent by weight) and additional nutrients were added resulting in a total amount of xylose of about 60 grams/liter. The propagation of the yeast continued for another 66 hours. In one of the reaction vessels, the pH was maintained (regulated) at 5.5; in the other reaction vessel the pH was unregulated. The samples were tested and analyzed for yeast growth (by dry weight), ethanol concentration, xylose concentration and optical density ($OD_{600}$) to evaluate xylose conversion. It was observed that the sample in which the pH was maintained at 5.5 produced more yeast than the sample in which pH was unregulated (within the indicated operating conditions). The results are shown in FIGS. 10A and 10B and TABLES 5A and 5B.

Example 1B

Figure 11A:
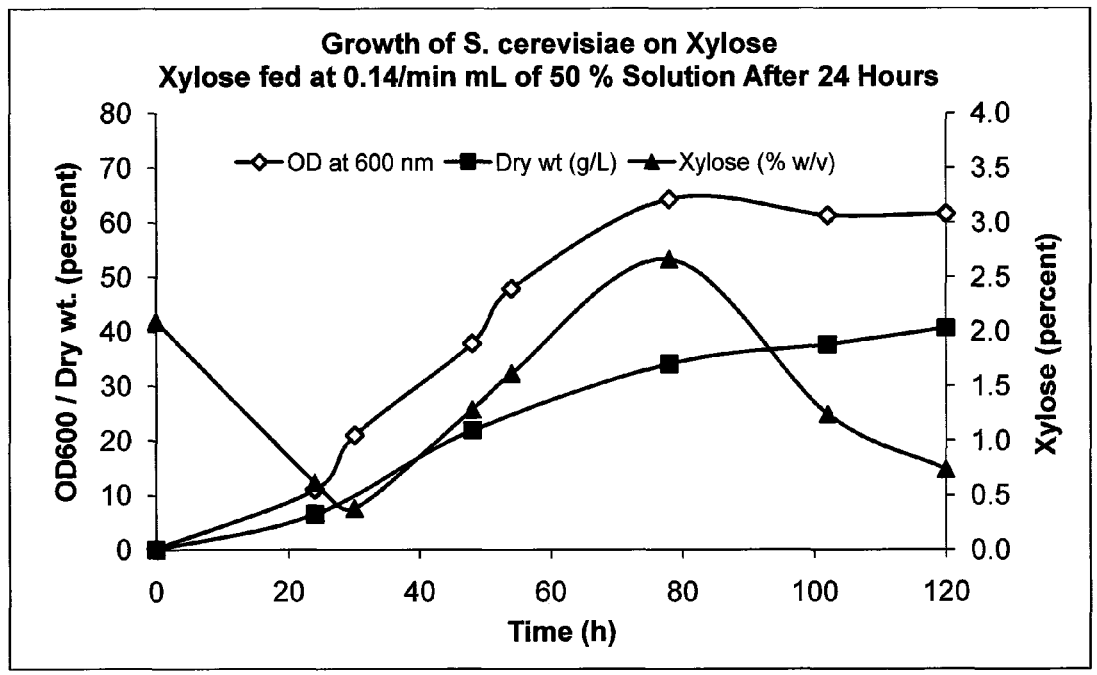
FIG. 11A is a line graph showing the growth of ethanologen.
Figure 11B:
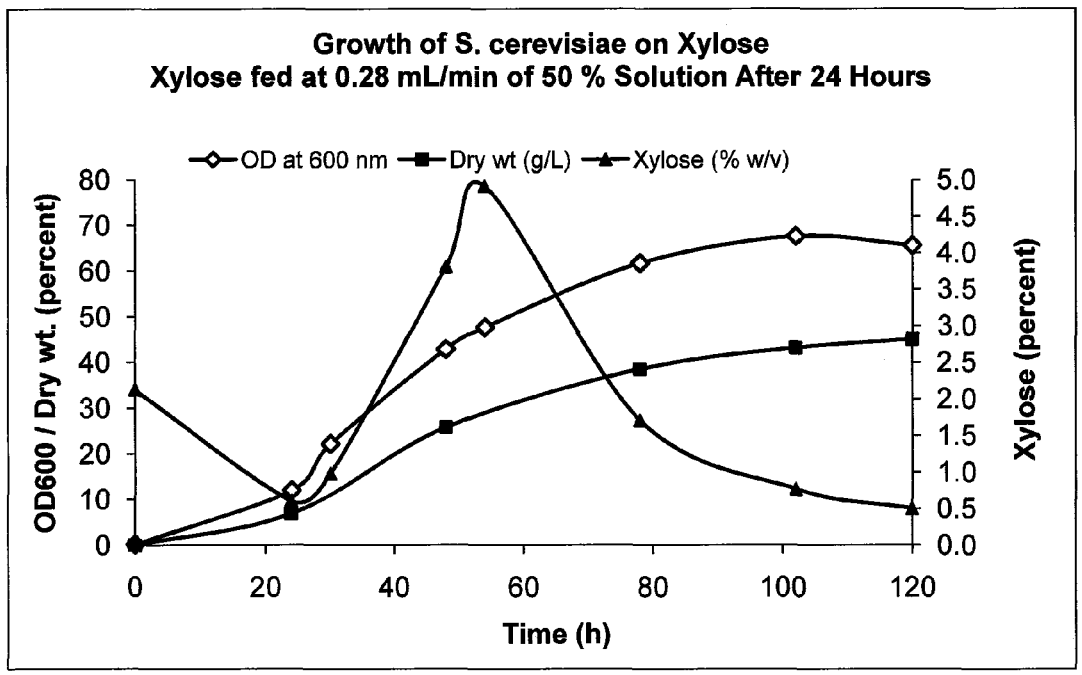
FIG. 11B is a line graph showing the growth of ethanologen.

The propagation system was used in Example 1B to evaluate the effect of feeding xylose at different rates on the growth of the ethanologen. The ethanologen was yeast (Strain No. RN1001). Samples were prepared in two separate reaction vessels. The samples comprised a medium (e.g. water and agents, such as nutrients, as indicated in TABLE 4) and the yeast inoculum. The samples also comprised xylose at a concentration of 20 grams per liter (of medium). The temperature of each reaction vessel was held at 30 degrees Celsius. The yeast was propagated in each reaction vessel for 24 hours. After 24 hours xylose solution (50 percent by weight, along with additional nutrients) was fed into one reaction vessel at 0.14 milliliters per minute for 46 hours resulting in a total xylose addition of 90 grams per liter, and into the other reaction vessel at 0.28 milliliters per minute for 46 hours resulting in a total amount of xylose of about 100 grams per liter. The propagation of the yeast continued for another 50 hours. The samples were tested and analyzed for yeast growth (by dry weight), ethanol concentration, xylose concentration and optical density ($OD_{600}$) to evaluate xylose conversion. It was observed that the samples exhibited similar yeast growth rates regardless of the rate of addition of xylose into the samples (within the indicated operating conditions). The results are shown in FIGS. 11A and 11B and TABLES 6A and 6B.

Example 2

Figure 12A:
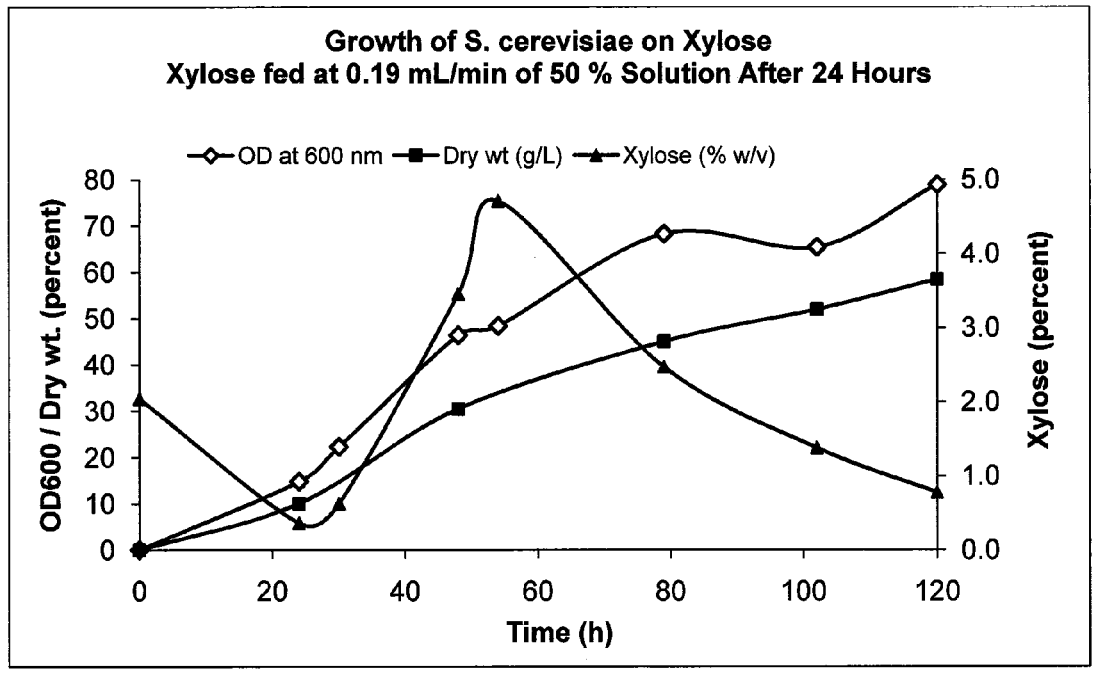
FIG. 12A is a line graph showing the growth of ethanologen using xylose.
Figure 12B:
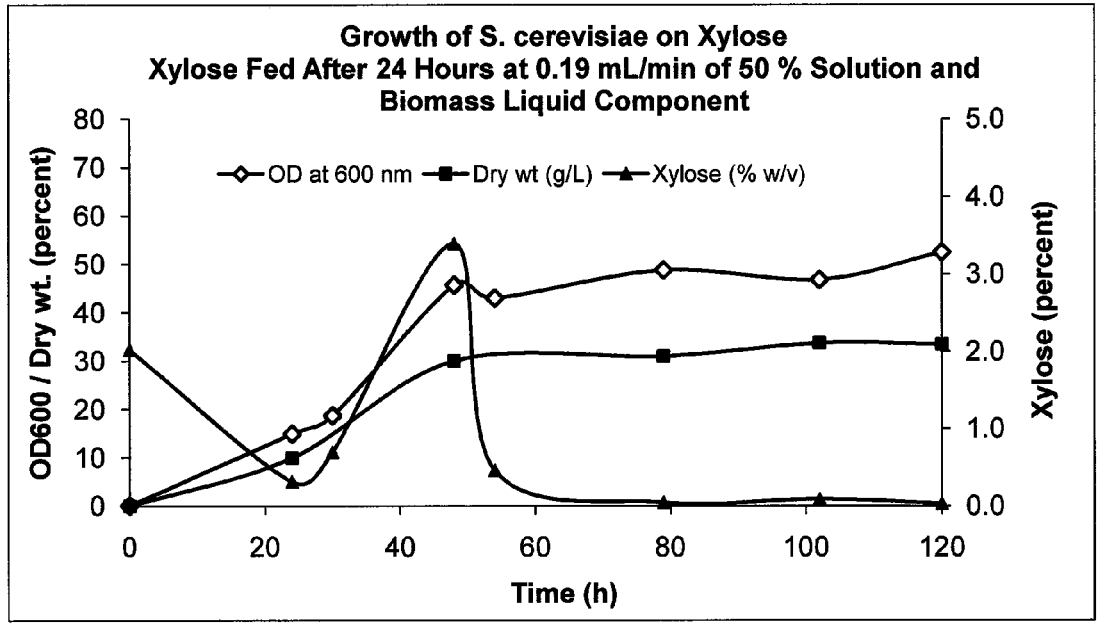
FIG. 12B is a line graph showing the growth of ethanologen using xylose and a biomass liquid component.
Figure 12C:
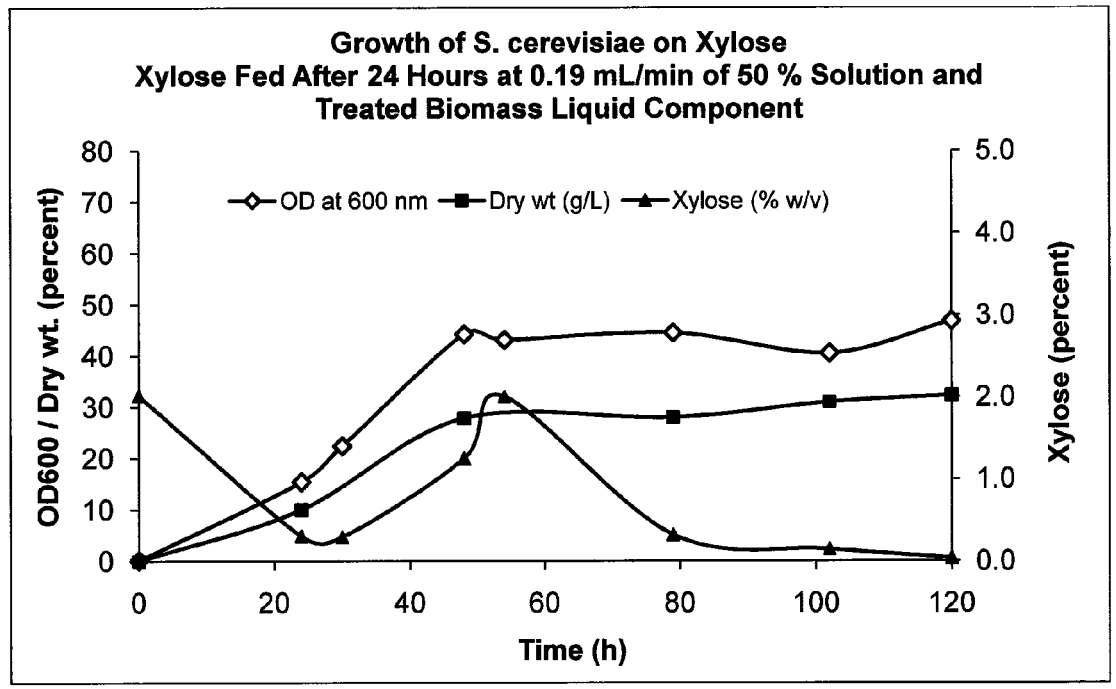
FIG. 12C is a line graph showing the growth of ethanologen using xylose and a treated biomass liquid component.

The propagation system was used in Example 2 to evaluate the effect of different sources of xylose on the growth of the ethanologen. A first biomass liquid component was prepared by dilute acid pre-treatment of corn cobs (see FIG. 6A and TABLES 2A and 2B). A treated biomass liquid component was prepared by treating the first liquid component by ion exchange chromatography. The ethanologen was yeast (Strain No. RN1001). Samples were prepared in three separate reaction vessels. The samples comprised a medium (e.g. water and agents, such as nutrients, as indicated in TABLE 4) and the yeast inoculum. The samples also comprised xylose at a concentration of 20 grams per liter (of medium). The pH of each sample was adjusted to and maintained (regulated) at 5.5. The temperature of each reaction vessel was held at 30 degrees Celsius. The yeast was propagated in each reaction vessel for 24 hours. After 24 hours the sample in the first reaction vessel was supplied with xylose solution (50 percent by weight, along with additional nutrients) at 0.19 milliliters per minute for 30 hours resulting in a total amount of xylose of about 106 grams per liter. The propagation of the yeast continued for another 66 hours. After 24 hours the sample in the second reaction vessel was supplied with xylose solution (50 percent by weight, along with additional nutrients) at 0.26 milliliters per minute for about 22 hours and after that with the biomass liquid component at 2.8 milliliters per minute for about 2.6 hours resulting in a total amount of xylose of about 95 grams per liter. The propagation of the yeast continued for another 71 hours. After 24 hours the sample in the third reaction vessel was supplied with xylose solution (50 percent by weight, along with additional nutrients) at 0.19 milliliters per minute for about 22 hours and after that with the treated biomass liquid component at 3.0 milliliters per minute for about 2 hours resulting in a total amount of xylose of about 92 grams per liter. The propagation of the yeast continued for another 72 hours. The samples were tested and analyzed for yeast growth (by dry weight), ethanol concentration, xylose concentration and optical density (at 600 nanometers [$OD_{600}$]) to evaluate xylose conversion. It was observed that xylose obtained from biomass (lignocellulosic plant material) could be used to propagate yeast (within the indicated operating conditions). The results are shown in FIGS. 12A through 12C and TABLES 7A through 7C.

Example 3

Figure 13A:
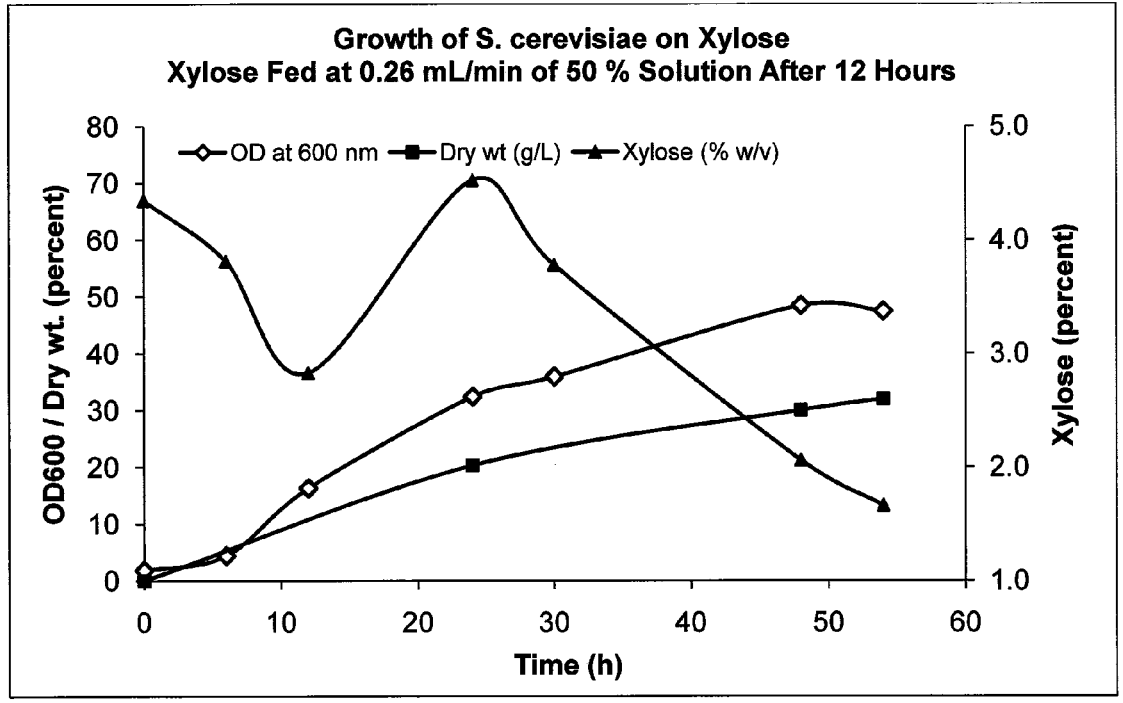
FIG. 13A is a line graph showing the growth of ethanologen using xylose during the second stage of a two-stage propagation.
Figure 13B:
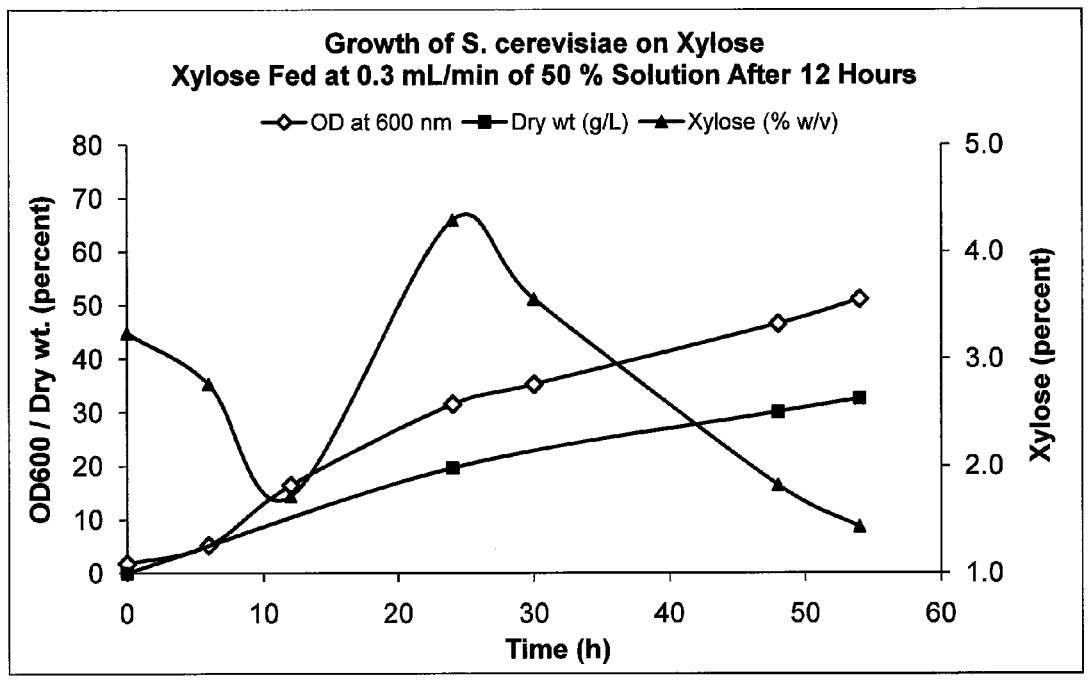
FIG. 13B is a line graph showing the growth of ethanologen using xylose during the second stage of a two-stage propagation.

The propagation system as indicated in FIGS. 7C and 9 was used in Example 3 to evaluate the growth of the ethanologen in a two-stage propagation system with differing xylose levels. The ethanologen was yeast (Strain No. RN1001). In the first stage a sample was prepared in a reaction vessel. The sample comprised medium (e.g. water and agents, such as nutrients, as indicated in TABLE 4) and the yeast inoculum. The sample also comprised xylose at a concentration of 20 grams per liter (of medium). The yeast was propagated for 24 hours. After 24 hours 300 mL of the sample from the first stage was used to inoculate each of two samples in two separate reaction vessels (stage two). The samples comprised medium (e.g. water and agents, such as nutrients, as indicated in TABLE 4) so that the total sample volume was 3 liters in each reaction vessel of the second stage. The sample in the first vessel of the second stage comprised xylose at a concentration of 40 grams per liter (of medium), and the sample in the second vessel of the second stage comprised xylose at a concentration of 30 grams per liter (of medium). The temperature of each reaction vessel was held at 30 degrees Celsius. The yeast was propagated in each reaction vessel for 12 hours. The pH of each sample was adjusted to and maintained (regulated) at 5.5. After 12 hours the sample in the first reaction vessel of the second stage was supplied with xylose solution (50 percent by weight, along with additional nutrients) at 0.26 milliliters per minute for 12 hours resulting in a total amount of xylose of about 64 grams per liter. The propagation of the yeast continued for another 30 hours. After 12 hours the sample in the second reaction vessel of the second stage was supplied with xylose solution (50 percent by weight, along with additional nutrients) at 0.30 milliliters per minute for about 12 hours resulting in a total amount of xylose of about 64 grams per liter. The propagation of the yeast continued for another 30 hours. It was observed that the total time to propagate yeast (e.g. yeast cell mass grown from approximately 0.04 grams to 20 grams in the first stage and from approximately 2 grams to 75 grams in the second stage) could be reduced in a two-stage propagation system (i.e. using approximately 78 hours) as compared to a one-stage propagation system (i.e. using approximately 100 to 120 hours). See also Examples 1A, 1B and 2. The results are shown in FIGS. 13A and 13B and TABLES 8A and 8B.

Example 4

Figure 14A:
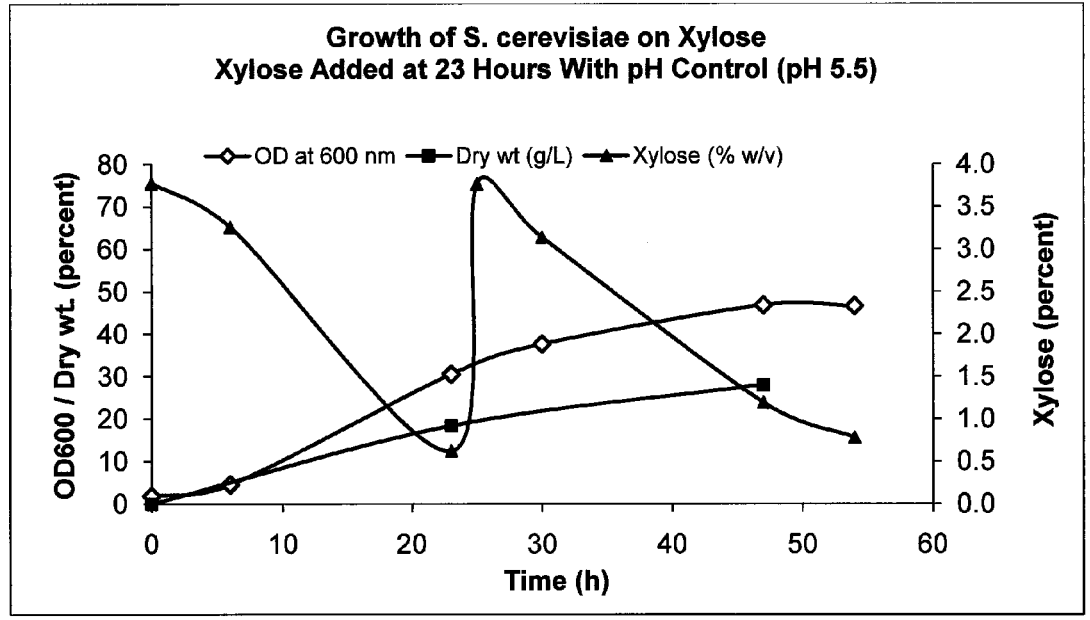
FIG. 14A is a line graph showing the growth of ethanologen using an initial loading of xylose during the second stage of a two-stage propagation.
Figure 14B:
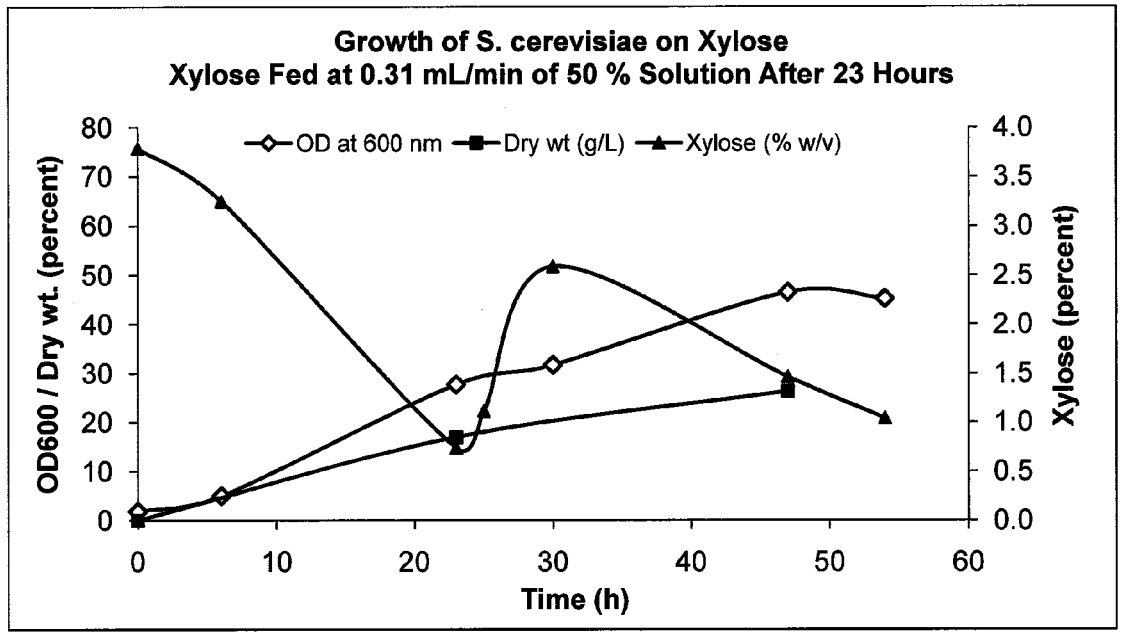
FIG. 14B is a line graph showing the growth of ethanologen using a continuous xylose feed during the second stage of a two-stage propagation.

The propagation system as indicated in FIGS. 7C and 9 was used in Example 4 to evaluate the effect of xylose feeding on the growth of the ethanologen. The ethanologen was yeast (Strain No. RN1014). In the first stage a sample was prepared in a reaction vessel. The sample comprised medium (e.g. water and agents, such as nutrients, as indicated in TABLE 4) and the yeast inoculum. The sample also comprised xylose at a concentration of 20 grams per liter (of medium). The yeast was propagated for 24 hours. After 24 hours 300 mL of the sample from the first stage was used to inoculate each of two samples in two separate reaction vessels (stage two). The samples comprised medium (e.g. water and agents, such as nutrients, as indicated in TABLE 4) so that the total sample volume was 3 liters in each reaction vessel of the second stage. Both samples of the second stage comprised xylose at a concentration of 35 grams per liter (of medium). The temperature of each reaction vessel was held at 30 degrees Celsius. The yeast was propagated in each reaction vessel for 23 hours. The pH of each sample was adjusted to and maintained (regulated) at 5.5. After 23 hours the sample in the first reaction vessel of the second stage was supplied with a single dose of xylose solution (50 percent by weight, along with additional nutrients) resulting in a total amount of xylose of about 64 grams per liter. The propagation of the yeast continued for another 31 hours. After 23 hours the sample in the second reaction vessel of the second stage was supplied with xylose solution (50 percent by weight, along with additional nutrients) at 0.31 milliliters per minute for about 8.2 hours resulting in a total amount of xylose of about 64 grams per liter. The propagation of the yeast continued for about another 32 hours. It was observed that the growth of yeast could be improved when additional xylose was supplied to the sample (i.e. after 23 hours) on a continuously-fed basis rather than in a single dose (within the indicated operating conditions). The results are shown in FIGS. 14A and 14B and TABLES 9A and 9B.

Example 5

Figure 15A:
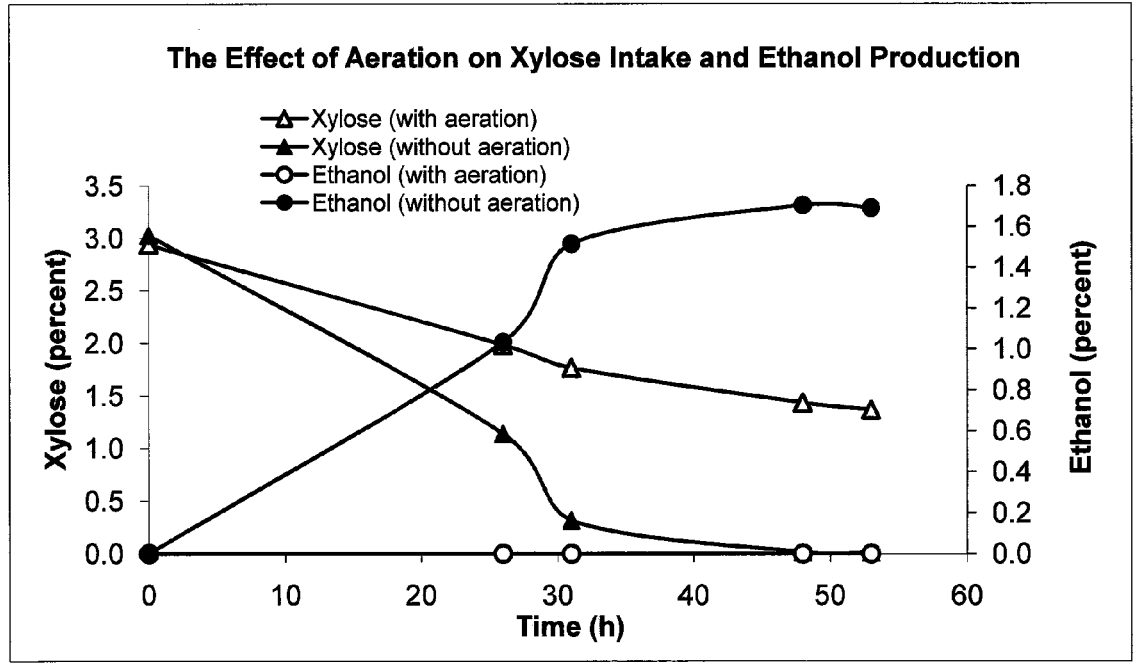
FIG. 15A is a line graph showing xylose consumption and ethanol production by ethanologen both with and without aeration.
Figure 15B:
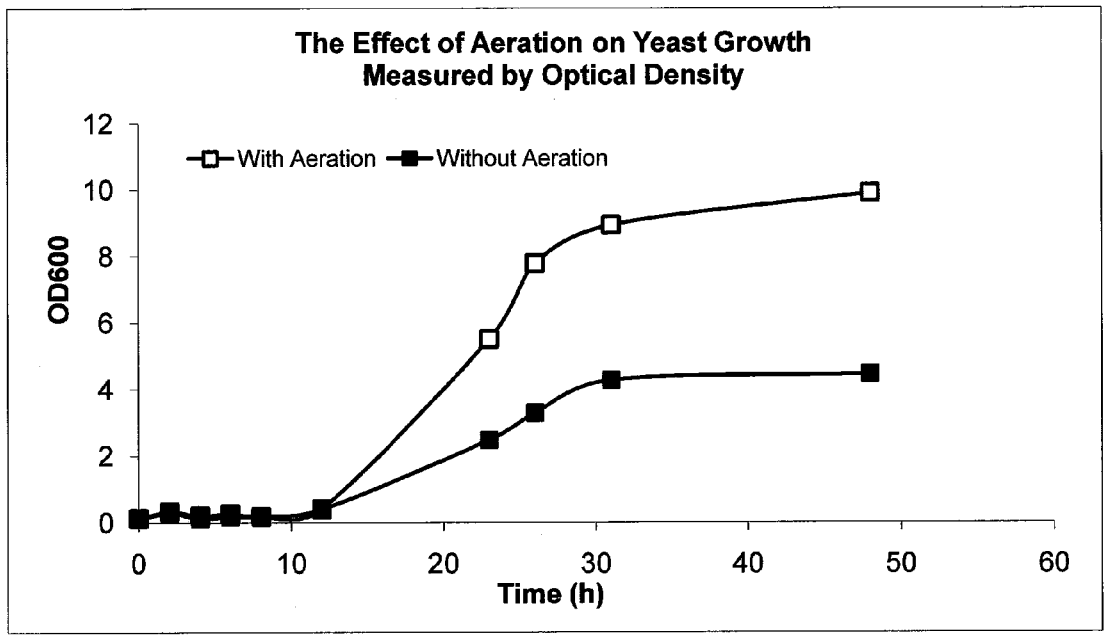
FIG. 15B is a line graph showing the growth of ethanologen both with and without aeration.

The propagation system was used in Example 5 to evaluate the effect of aeration on the growth of the ethanologen. The ethanologen was yeast (Strain No. RWB218). Samples were prepared in two separate reaction vessels. The samples comprised medium (e.g. water and agents, such as nutrients, as indicated in TABLE 4) and the yeast inoculum. The samples also comprised xylose at a concentration of 30 grams per liter (of medium). One reaction vessel was aerated at 5 liters per minute; the other reaction vessel was not aerated. The yeast was propagated in each reaction vessel at 32 degrees Celsius for 53 hours. The samples were tested and analyzed for yeast growth (by dry weight), ethanol concentration, xylose concentration and optical density ($OD_{600}$) to evaluate xylose conversion. It was observed that the growth of yeast could be improved when the sample was aerated (within the indicated operating conditions) insofar as the yeast used the supplied xylose for cell mass growth rather than for the production of ethanol. The results are shown in FIGS. 15A and 15B and TABLES 10A and 10B.

Example 6

Figure 16A:
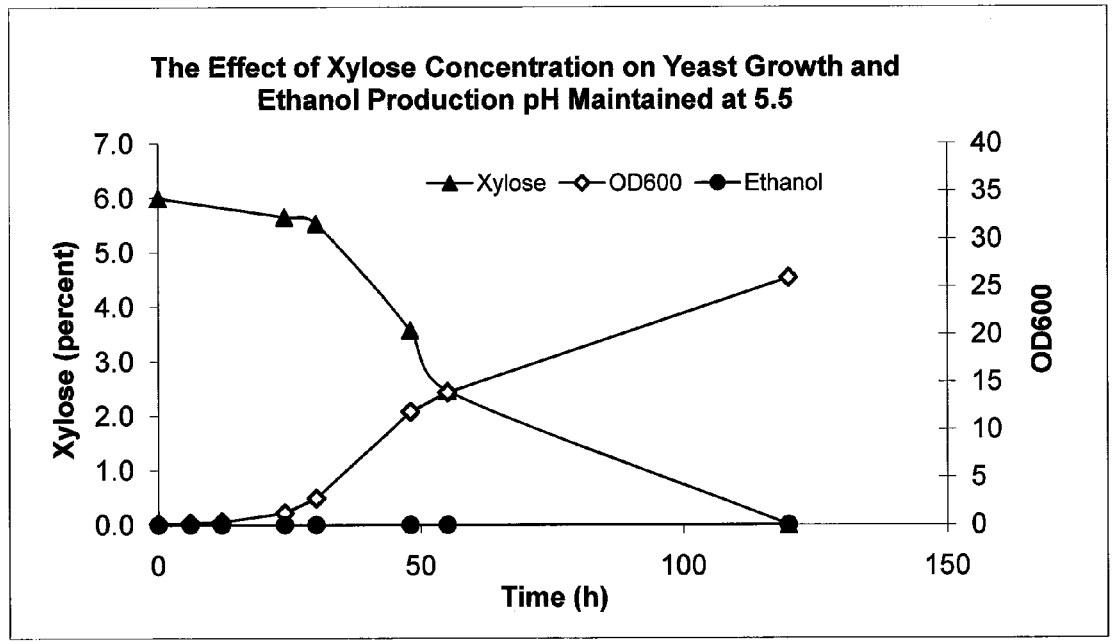
FIG. 16A is a graph showing the growth of ethanologen using xylose.
Figure 16B:
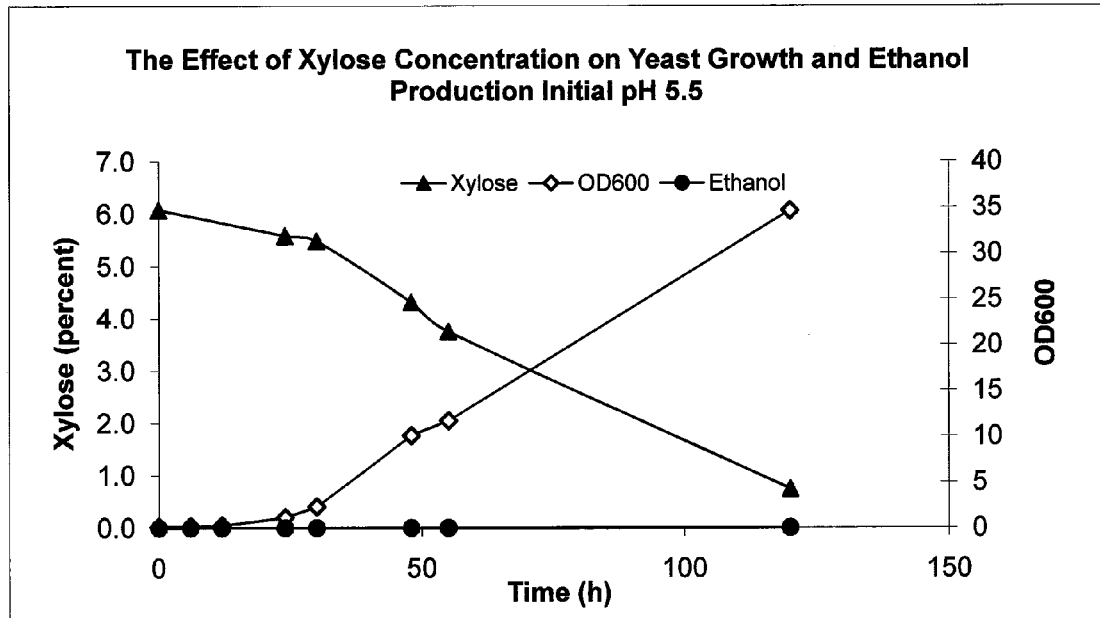
FIG. 16B is a graph showing growth of ethanologen using xylose.
Figure 16C:
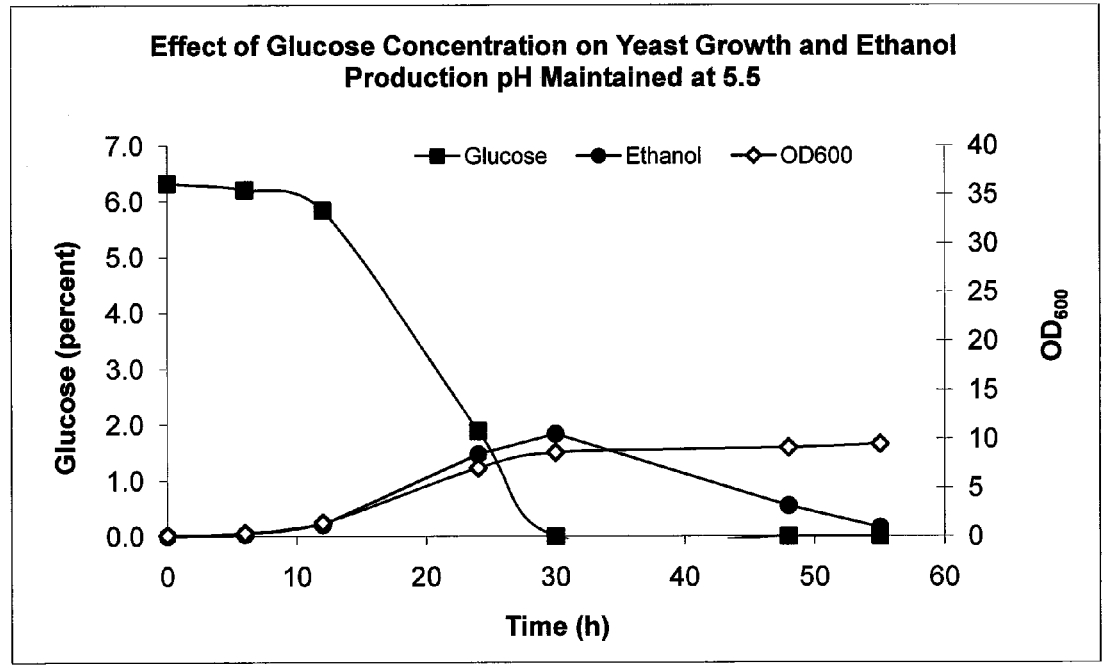
FIG. 16C is a graph showing growth of ethanologen using glucose.

The propagation system was used in Example 6 to evaluate the effect of xylose and glucose concentrations on the growth of the ethanologen. The ethanologen was yeast (Strain No. RWB218). Samples were prepared in three separate reaction vessels. The samples comprised medium (e.g. water and agents, such as nutrients, as indicated in TABLE 11A) and the yeast inoculum. The temperature of each reaction vessel was held at 32 degrees Celsius. Each reaction vessel was aerated at 4.5 liters per minute. The first and second reaction vessels were supplied with xylose at a concentration of 60 grams per liter; the third reaction vessel was supplied with glucose at a concentration of 60 grams per liter. The pH of the samples in the second and third reaction vessels was adjusted to and maintained (regulated) at 5.5. The yeast was propagated in the first and second reaction vessel at 32 degrees Celsius for 120 hours. The yeast was propagated in the third reaction vessel at 32 degrees Celsius for 52 hours. It was observed that the growth of yeast could be improved when the sample was aerated insofar as the yeast used the supplied xylose for cell mass growth rather than the production of ethanol, notwithstanding the concentration of xylose (within the indicated operating conditions). The results are shown in FIGS. 16A through 16C and TABLES 11A through 11C.

The embodiments as disclosed and described in the application (including the FIGURES and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

TABLE 1A

Biomass Composition

| Cob (percent) | Husks/Leaves (percent) | Stalk (percent) | Cellulose (Glucan) (percent) | Hemicellulose Xylan (percent) | Hemicellulose Arabinan (percent) | Hemicellulose Acetate (percent) | Hemicellulose Composite (percent) | Lignin (percent) | Ash (percent) |
| --- | --- | --- | --- | --- | --- | --- | --- | --- | --- |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

TABLE 1B

Biomass Typical and Expected Composition

| | Cellulose (Glucan) (percent) (approx.) | Hemicellulose (percent) (approx.) | Lignin (percent) (approx.) | Ash (percent) (approx.) |
| --- | --- | --- | --- | --- |
| Typical Range | 35-45 | 24-42 | 12-20 | 2-8 |
| Expected Range | 30-55 | 20-50 | 10-25 | 1-10 |

TABLE 2A

Pre-Treated Biomass Liquid Component Composition

| Cob (percent) | Husks/Leaves (percent) | Stalk (percent) | Glucose (percent) | Xylose (percent) | Arabinose (percent) | Acetic Acid (ppm) |
| --- | --- | --- | --- | --- | --- | --- |
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 30 | 50 | 20 | 0.4 | 3.6 | 0.5 | 4763 |

TABLE 2B

Pre-Treated Biomass Liquid Component Typical and Expected Composition

| | Glucose (percent) (approx.) | Xylose (percent) (approx.) | Arabinose (percent) (approx.) | Acetic Acid (ppm) (approx.) |
| --- | --- | --- | --- | --- |
| Typical Range | 0-1 | 2-6 | 0-1 | 3000-6400 |
| Expected Range | 0-1 | 1-8 | 0-1 | 2000-8000 |

TABLE 3A

Pre-Treated Biomass Solids Component Composition

| Cob (percent) | Husks/Leaves (percent) | Stalk (percent) | Cellulose (Glucan) (percent) | Xylan (percent) | Hemicellulose Arabinan (percent) | Acetate (percent) | Composite (percent) | Lignin (percent) | Ash (percent) |
|---|---|---|---|---|---|---|---|---|---|
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 30 | 50 | 20 | 55.5 | 3.8 | 0.8 | 0.6 | 11.5 | 25.4 | 5.8 |

TABLE 3B

Pre-Treated Biomass Solids Component Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

TABLE 4

Growth Medium Composition

| Component | Concentration* |
|---|---|
| Yeast Extract | 5 g/L |
| Urea | 10 g/L |
| Diammonium Phosphate | 2.5 g/L |
| Magnesium Sulfate Heptahydrate | 0.5 g/L |
| Zinc Sulfate Heptahydrate | 0.02 g/L |
| Lactoside 247 | 5 PPM |

*In Water

TABLE 5A

| Time (h) | $OD_{600}$ | Dry cell wt. (g/L) | Xylose (% w/v) |
|---|---|---|---|
| 0 | 0.1 | NT | 3.16 |
| 24 | 16.5 | 10.78 | 1.18 |
| 30 | 26.6 | NT | 0.29 |
| 48 | 28.2 | 17.21 | 0.01 |
| 54 | 29.0 | NT | 3.06 |
| 78 | 49.2 | 27.67 | 0.55 |
| 102 | 47.1 | 30.53 | 0.20 |
| 120 | 46.3 | 31.84 | 0.13 |

$OD_{600}$ - Optical density at 600 nm
NT - Not tested

TABLE 5B

| Time (h) | $OD_{600}$ | Dry cell wt. (g/L) | Xylose (% w/v) |
|---|---|---|---|
| 0 | 0.1 | NT | 3.31 |
| 24 | 12.4 | 7.23 | 1.59 |
| 30 | 15.6 | NT | 1.44 |
| 48 | 14.6 | 8.55 | 1.20 |
| 54 | 19.7 | NT | 3.90 |
| 78 | 29.5 | 16.35 | 2.39 |
| 102 | 34.1 | 16.77 | 1.88 |
| 120 | 33.1 | 17.04 | 1.71 |

$OD_{600}$—Optical density at 600 nm
NT—Not tested

TABLE 6A

| Time (h) | $OD_{600}$ | Dry cell wt. (g/L) | Xylose (% w/v) |
|---|---|---|---|
| 0 | 0.2 | NT | 2.09 |
| 24 | 11.0 | 6.52 | 0.61 |
| 30 | 21.0 | NT | 0.38 |
| 48 | 37.8 | 21.88 | 1.29 |
| 54 | 47.9 | NT | 1.62 |
| 78 | 64.3 | 34.06 | 2.66 |
| 102 | 61.3 | 37.65 | 1.24 |
| 120 | 61.6 | 40.64 | 0.74 |

$OD_{600}$—Optical density at 600 nm
NT—Not tested

TABLE 6B

| Time (h) | $OD_{600}$ | Dry cell wt. (g/L) | Xylose (% w/v) |
|---|---|---|---|
| 0 | 0.1 | NT | 2.13 |
| 24 | 12.0 | 6.92 | 0.61 |
| 30 | 22.2 | NT | 0.98 |
| 48 | 42.9 | 25.79 | 3.81 |
| 54 | 47.7 | NT | 4.92 |
| 78 | 61.7 | 38.5 | 1.71 |
| 102 | 67.6 | 43.21 | 0.77 |
| 120 | 65.6 | 45.11 | 0.50 |

$OD_{600}$—Optical densty at 600 nm
NT—Not tested

TABLE 7A

| Time (h) | $OD_{600}$ | Dry cell wt. (g/L) | Xylose (% w/v) |
|---|---|---|---|
| 0 | 0.0 | NT | 2.04 |
| 24 | 14.8 | 10.08 | 0.36 |
| 30 | 22.3 | NT | 0.63 |
| 48 | 46.4 | 30.46 | 3.46 |
| 54 | 48.4 | NT | 4.71 |
| 79 | 68.3 | 45.00 | 2.47 |

TABLE 7A-continued

| Time (h) | OD$_{600}$ | Dry cell wt. (g/L) | Xylose (% w/v) |
|---|---|---|---|
| 102 | 65.4 | 51.91 | 1.38 |
| 120 | 78.9 | 58.40 | 0.78 |

OD$_{600}$—Optical density at 600 nm
NT—Not tested

TABLE 7B

| Time (h) | OD$_{600}$ | Dry cell wt. (g/L) | Xylose (% w/v) |
|---|---|---|---|
| 0 | 0.1 | NT | 2.02 |
| 24 | 14.9 | 9.97 | 0.31 |
| 30 | 18.7 | NT | 0.70 |
| 48 | 45.7 | 30.04 | 3.39 |
| 54 | 43.0 | NT | 0.46 |
| 79 | 48.8 | 31.00 | 0.05 |
| 102 | 46.8 | 33.72 | 0.09 |
| 120 | 52.5 | 33.45 | 0.03 |

OD$_{600}$—Optical density at 600 nm
NT—Not tested

TABLE 7C

| Time (h) | OD$_{600}$ | Dry cell wt. (g/L) | Xylose (% w/v) |
|---|---|---|---|
| 0 | 0.1 | NT | 2.02 |
| 24 | 15.4 | 10.01 | 0.30 |
| 30 | 22.4 | NT | 0.30 |
| 48 | 44.2 | 27.85 | 1.25 |
| 54 | 43.1 | NT | 2.01 |
| 79 | 44.5 | 28.00 | 0.32 |
| 102 | 40.5 | 30.99 | 0.15 |
| 120 | 46.8 | 32.29 | 0.04 |

OD$_{600}$—Optical density at 600 nm
NT—Not tested

TABLE 8A

| Time (h) | OD$_{600}$ | Dry cell wt. (g/L) | Xylose (% w/v) |
|---|---|---|---|
| 0 | 1.8 | NT | 4.35 |
| 6 | 4.4 | NT | 3.81 |
| 12 | 16.3 | NT | 2.83 |
| 24 | 32.4 | 20.33 | 4.53 |
| 30 | 35.9 | NT | 3.78 |
| 48 | 48.4 | 30.00 | 2.06 |
| 54 | 47.4 | 31.99 | 1.66 |

OD$_{600}$—Optical density at 600 nm
NT—Not tested

TABLE 8B

| Time (h) | OD$_{600}$ | Dry cell wt. (g/L) | Xylose (% w/v) |
|---|---|---|---|
| 0 | 1.8 | NT | 3.24 |
| 6 | 5.2 | NT | 2.76 |
| 12 | 16.4 | NT | 1.72 |
| 24 | 31.5 | 19.63 | 4.29 |
| 30 | 35.9 | NT | 3.56 |
| 48 | 46.5 | 30.07 | 1.82 |
| 54 | 51.1 | 32.55 | 1.43 |

OD$_{600}$—Optical density at 600 nm
NT—Not tested

TABLE 9A

| Time (h) | OD$_{600}$ | Dry cell wt. (g/L) | Xylose (% w/v) |
|---|---|---|---|
| 0 | 1.8 | NT | 3.78 |
| 6 | 4.5 | NT | 3.26 |
| 23 | 30.5 | 18.38 | 0.62 |
| 25 | NT | NT | 3.77 |
| 30 | 37.6 | NT | 3.14 |
| 47 | 46.8 | 27.97 | 1.19 |
| 54 | 46.6 | NT | 0.78 |

OD$_{600}$—Optical density at 600 nm
NT—Not tested

TABLE 9B

| Time (h) | OD$_{600}$ | Dry cell wt. (g/L) | Xylose (% w/v) |
|---|---|---|---|
| 0 | 1.8 | NT | 3.79 |
| 6 | 5.0 | NT | 3.25 |
| 23 | 27.7 | 16.99 | 0.74 |
| 25 | NT | NT | 1.12 |
| 30 | 31.7 | NT | 2.59 |
| 47 | 46.5 | 26.31 | 1.46 |
| 54 | 45.2 | NT | 1.04 |

OD$_{600}$—Optical density at 600 nm
NT—Not tested

TABLE 10A

| | Xylose (percent, by weight) | | Ethanol (percent, by volume) | |
|---|---|---|---|---|
| Time (h) | With Aeration | No Aeration | With Aeration | No Aeration |
| 0 | 2.94 | 3.03 | 0.00 | 0.00 |
| 26 | 1.98 | 1.14 | 0.00 | 1.03 |
| 31 | 1.76 | 0.32 | 0.00 | 1.52 |
| 48 | 1.43 | 0.02 | 0.00 | 1.70 |
| 53 | 1.37 | 0.01 | 0.00 | 1.69 |

TABLE 10B

| | Optical Density at 600 nm | |
|---|---|---|
| Time (h) | With Aeration | No Aeration |
| 0 | 0.13 | 0.10 |
| 2 | 0.32 | 0.28 |
| 4 | 0.20 | 0.11 |
| 6 | 0.26 | 0.17 |
| 8 | 0.18 | 0.19 |
| 12 | 0.41 | 0.39 |
| 23 | 5.51 | 2.47 |
| 26 | 7.78 | 3.29 |
| 31 | 8.93 | 4.27 |
| 48 | 9.90 | 4.45 |

TABLE 11A

Growth Medium Composition

| Component | Concentration |
|---|---|
| Yeast Extract | 5 g/L |
| Urea | 20 g/L |
| Diammonium Phosphate | 5.0 g/L |

-continued

| Growth Medium Composition | |
|---|---|
| Component | Concentration |
| Magnesium Sulfate Heptahydrate | 0.8 g/L |
| Zinc Sulfate Heptahydrate | 0.03 g/L |
| Lactoside 247 | 5 PPM |

* In Water

TABLE 11B

| Time (h) | $OD_{600}$ | Dry cell wt. (g/L) | Xylose (percent) |
|---|---|---|---|
| 0 | 1.8 | NT | 3.79 |
| 6 | 5.0 | NT | 3.25 |
| 23 | 27.7 | 16.99 | 0.74 |
| 25 | NT | NT | 1.12 |
| 30 | 31.7 | NT | 2.59 |
| 47 | 46.5 | 26.31 | 1.46 |
| 54 | 45.2 | NT | 1.04 |

$OD_{600}$—Optical density at 600 nm
NT—Not tested

TABLE 11C

| Time (h) | $OD_{600}$ | Dry cell wt. (g/L) | Xylose (percent) |
|---|---|---|---|
| 0 | 1.7 | NT | 3.69 |
| 6 | 5.1 | NT | 3.20 |
| 23 | 31.8 | 19.07 | 0.29 |
| 25 | NT | NT | 0.79 |
| 30 | 38.1 | NT | 1.92 |
| 47 | 46 | 27.41 | 0.62 |
| 52 | 49.1 | NT | 0.43 |

$OD_{600}$—Optical density at 600 nm
NT—Not tested

We claim:

1. A method of propagating ethanologen for use in the production of ethanol from biomass comprising the steps of:
   providing a medium for propagation of ethanologen;
   supplying a first cell mass of ethanologen to the medium;
   supplying xylose to the medium as a carbon source for cell mass growth of the ethanologen;
   maintaining the medium comprising the first cell mass of ethanologen at a pH of between about 5.0 and 6.0 and at a temperature of between about 26 and about 37 degrees Celsius so that the first cell mass of ethanologen is propagated into a second cell mass of ethanologen, under aerobic conditions with an airflow of at least 1.0 volumes of air per volume of medium per minute;
   and wherein the second cell mass of ethanologen is larger than the first cell mass of ethanologen.

2. The method of claim 1 wherein xylose is the sole source of carbon supplied to the medium.

3. The method of claim 2 wherein the ethanologen is derived from *Saccharomyces cerevisiae*.

4. The method of claim 2 wherein the ethanologen comprises yeast, and the second cell mass of ethanologen comprises about 0.35 to 0.55 grams dry yeast per gram of sugar.

5. The method of claim 2 wherein xylose is supplied to the medium at a concentration of at least 1 percent by weight of medium.

6. The method of claim 2 wherein xylose is supplied to the medium at a concentration of at least 3 percent by weight of medium.

7. The method of claim 2 wherein xylose is supplied to the medium at a concentration of about 6 percent by weight of medium.

8. The method of claim 2 wherein the step of providing a first medium for propagation of the ethanologen comprises a first stage and further comprising the steps of:
   providing a second medium for propagation of ethanologen in a second stage;
   supplying the second cell mass of ethanologen to the second medium;
   maintaining the second medium comprising the second cell mass of ethanologen at a pH of between about 5.0 and 6.0 and at a temperature of between about 26 and about 37 degrees Celsius so that the second cell mass of ethanologen is propagated into a third cell mass of ethanologen;
   wherein the third cell mass of ethanologen has a cell mass that is larger than the cell mass of the second cell mass of ethanologen.

9. The method of claim 8 wherein xylose is provided to the second medium as a carbon source for the ethanologen in the second stage.

10. The method of claim 8 wherein the third cell mass is at least 20 times larger than the second cell mass.

11. The method of claim 8 wherein the second cell mass is at least 200 times larger than the first cell mass.

12. The method of claim 11 wherein the propagation of the first cell mass of ethanologen into the second cell mass of ethanologen and the propagation of the second ethanologen into the third cell mass of ethanologen comprise a total time of no more than about 80 hours.

13. The method of claim 1 wherein the biomass comprises lignocellulosic material.

14. The method of claim 13 wherein the lignocellulosic material comprises at least one of corn cobs, corn plant husks, corn plant leaves and corn plant stalks.

15. The method of claim 13 wherein the xylose supplied to the medium is obtained from the lignocellulosic material.

16. The method of claim 15 wherein xylose is obtained as a component of the biomass and wherein xylose is supplied to the medium comprises at a rate of at least 0.12 grams of xylose per minute.

17. The method of claim 16 wherein the component comprises xylose at about 2 to 5 percent by weight.

18. The method of claim 16 wherein the component comprises xylose and glucose and the ethanologen comprises an organism capable of fermenting xylose into ethanol and glucose into ethanol.

19. The method of claim 18 wherein the ethanologen comprises *Saccharomyces cerevisiae*.

20. The method of claim 1 wherein the ethanologen comprises yeast cells capable of fermenting pentose into ethanol.

21. The method of claim 1 wherein the ethanologen comprises yeast cells capable of fermenting xylose into ethanol.

22. The method of claim 1 wherein xylose has been used as a carbon source for growth of the second cell mass of ethanologen.

23. The method of claim 22 wherein the use of xylose for growth of the first cell mass into the second cell mass of ethanologen is such that at least 80 percent of the xylose is consumed.

24. The method of claim 1 wherein the second cell mass of ethanologen comprises an inoculum of the ethanologen that can be provided to a fermentation system for fermentation of pentose.

25. The method of claim 1 further comprising the step of providing an agent to the medium; wherein the agent comprises at least one nutrient.

26. The method of claim 25 wherein the agent comprises at least one of yeast extract, urea, diammonium phosphate, magnesium sulfate or zinc sulfate.

27. The method of claim 1 wherein the ethanologen comprises a strain of Saccharomyces cerevisiae capable of converting xylose into ethanol.

28. The method of claim 1 wherein the step of maintaining the medium comprises applying xylose to the medium and maintaining the medium at about 30 degrees Celsius for about 120 hours.

29. The method of claim 1 wherein the step of maintaining the medium comprises aerating a yeast inoculum.

30. The method of claim 1 wherein the biomass comprises hemicellulose and the fermentation product has been produced by fermentation of xylose.

31. The method of claim 1 wherein the biomass comprises cellulose and the fermentation product has been produced by fermentation of glucose.

32. A method of propagating ethanologen for use in the production of ethanol from biomass comprising the steps of:
providing a medium for propagation of ethanologen;
supplying a first cell mass of ethanologen to the medium;
providing an agent to the medium;
providing a component obtained from the biomass to the medium as a carbon source for the ethanologen;
maintaining the medium comprising the first cell mass of ethanologen at a pH of between about 5.0 and 6.0 and at a temperature of between about 26 and about 37 degrees Celsius so that the first cell mass of ethanologen is propagated into a second cell mass of ethanologen, wherein the medium comprising the ethanologen is aerated with an airflow of at least 1.0 volumes of air per volume of medium per minute;
wherein the second cell mass of ethanologen is larger than the first cell mass of ethanologen;
wherein the biomass comprises lignocellulosic material;
wherein the lignocellulosic material comprises at least one of corn cobs, corn plant husks, corn plant leaves and corn plant stalks;
wherein the component is obtained from the lignocellulosic material;
wherein the component comprises pentose;
wherein pentose comprises the carbon source for the ethanologen; and
wherein the ethanologen comprises yeast cells capable of fermenting pentose into ethanol.

33. The method of claim 32 wherein the second cell mass of ethanologen comprises an inoculum of the ethanologen that can be provided to a fermentation system for fermentation of pentose.

34. The method of claim 32 wherein pentose comprises xylose.

35. The method of claim 34 wherein the component comprises xylose at about 2 to 5 percent by weight.

36. The method of claim 34 wherein the biomass comprises hemicellulose and the fermentation product has been produced by fermentation of xylose.

37. The method of claim 34 wherein the biomass comprises hemicellulose and the fermentation product has been produced by fermentation of glucose.

38. The method of claim 32 wherein the ethanologen comprises a strain of Saccharomyces cerevisiae capable of converting xylose into ethanol.

39. The method of claim 32 wherein the step of maintaining the medium comprises applying the component to the medium and maintaining the medium at about 30 degrees Celsius for about 120 hours.

40. The method of claim 39 wherein the medium comprises sugar, the ethanologen comprises yeast and the second cell mass of ethanologen comprises about 0.35 to 0.55 grams dry yeast per gram of sugar.

41. The method of claim 32 wherein the agent comprises at least one of yeast extract, urea, diammonium phosphate, magnesium sulfate, zinc sulfate.

42. The method of claim 32 wherein the step of supplying the component to the medium comprises xylose supplied at a rate of at least 0.12 grams of xylose per minute.

43. The method of claim 32 wherein the component comprises xylose and glucose and the ethanologen comprises an organism capable of fermenting xylose into ethanol and glucose into ethanol.

44. The method of claim 43 wherein the ethanologen comprises Saccharomyces cerevisiae.

45. The method of claim 32 further comprising the steps of:
providing a second medium for propagation of ethanologen;
supplying the second cell mass of ethanologen to the second medium;
maintaining the second medium comprising the second cell mass of ethanologen at a pH of between about 5.0 and 6.0 and at a temperature of between about 26 and about 37 degrees Celsius so that the second cell mass of ethanologen is propagated into a third cell mass of ethanologen;
wherein the third cell mass of ethanologen has a cell mass that is larger than the cell mass of the second cell mass of ethanologen.

46. The method of claim 45 wherein the propagation of the first cell mass of ethanologen into the second cell mass of ethanologen and the propagation of the second ethanologen into the third cell mass of ethanologen comprise a total time of no more than about 80 hours.

47. A system for propagating ethanologen for use in the production of ethanol from biomass in a fermentation system comprising:
a first stage comprising a first vessel configured to maintain a medium comprising ethanologen;
a second stage comprising a second vessel configured to maintain a medium supplied from the first stage;
a source of xylose to be provided to the medium as a carbon source for ethanologen in the first stage;
a source of xylose to be provided to the medium as a carbon source for the ethanologen in the second stage;
wherein the ethanologen has a first cell mass when supplied to the first stage and the ethanologen has a second cell mass when supplied from the first stage to the second stage and the ethanologen has a third cell mass when supplied from the second stage;
wherein the medium in the first vessel is maintained at a pH of between about 5.0 and 6.0 and at a temperature of between about 26 and about 37 degrees Celsius with an airflow of at least 1.0 volumes of air per volume of medium per minute so that ethanologen can be propagated into the second cell mass;
wherein the medium in the second vessel is maintained at a pH of between about 5.0 and 6.0 and at a temperature of between about 26 and about 37 degrees Celsius with an airflow of at least 1.0 volumes of air per volume of medium per minute so that ethanologen can be propagated into the third cell mass;

wherein the second cell mass is at least 200 times larger than the first cell mass;

wherein the third cell mass is at least 20 times larger than the second cell mass.

48. The system of claim 47 further comprising an apparatus to pre-treat the biomass into a liquid component comprising the source of xylose for the ethanologen.

49. A method of propagating ethanologen for use in the production of ethanol from biomass comprising the steps of:
providing a medium for propagation of ethanologen;
supplying a first cell mass of ethanologen having a first cell mass to the medium;
supplying xylose to the medium as a carbon source for the ethanologen;
maintaining the medium comprising the first cell mass of ethanologen at a pH of between about 5.0 and 6.0 and at a temperature of between about 26 and about 37 degrees Celsius under aerobic conditions so that the first cell mass of ethanologen is propagated into a second cell mass of ethanologen, under aerobic conditions comprises a supply of air of at least 1.0 liters per liter of medium per minute so that xylose is used for cell growth instead of production of ethanol;
and wherein the second cell mass of ethanologen is larger than the first cell mass of ethanologen.

50. The method of claim 49 wherein xylose is the sole source of carbon supplied to the medium.

51. The method of claim 49 wherein xylose is supplied to the medium at a concentration of at least 3 percent (by weight in medium).

52. The method of claim 49 wherein xylose is supplied to the medium at a concentration of about 6 percent (by weight in medium).

53. The method of claim 49 wherein the biomass comprises lignocellulosic material.

* * * * *